United States Patent [19]

Gordon et al.

[11] Patent Number: 4,514,391

[45] Date of Patent: Apr. 30, 1985

[54] HYDROXY SUBSTITUTED PEPTIDE COMPOUNDS

[75] Inventors: Eric M. Gordon, Pennington; Jollie D. Godfrey, Jr., Lawrenceville; Sesha I. Natarajan, Neshanic Station, all of N.J.

[73] Assignee: E. R. Squibb & Sons, Inc., Princeton, N.J.

[21] Appl. No.: 515,729

[22] Filed: Jul. 21, 1983

[51] Int. Cl.³ .................... A61K 37/00; C07C 103/52
[52] U.S. Cl. ................... 514/2; 260/112.5 K
[58] Field of Search ............... 260/112.5 R; 424/177

[56] References Cited

U.S. PATENT DOCUMENTS

| | | | |
|---|---|---|---|
| 4,105,776 | 8/1978 | Ondetti et al. | 424/274 |
| 4,129,566 | 12/1978 | Ondetti et al. | 546/326 |
| 4,154,935 | 5/1979 | Ondetti et al. | 546/189 |
| 4,192,878 | 3/1980 | Ondetti | 424/270 |
| 4,199,512 | 4/1980 | Ondetti et al. | 260/326.12 R |
| 4,217,359 | 8/1980 | Krapcho | 424/274 |
| 4,234,489 | 11/1980 | Ondetti et al. | 260/326.42 |
| 4,256,751 | 3/1981 | Hayashi et al. | 424/258 |
| 4,296,033 | 10/1981 | Petrillo et al. | 260/326.2 |
| 4,296,113 | 10/1981 | Ondetti | 424/246 |
| 4,311,697 | 1/1982 | Krapcho | 424/240 |
| 4,316,905 | 2/1982 | Krapcho | 424/274 |
| 4,316,906 | 2/1982 | Ondetti et al. | 424/274 |
| 4,374,829 | 2/1983 | Harris et al. | 424/177 |
| 4,470,973 | 9/1984 | Natarajan et al. | 424/177 |

FOREIGN PATENT DOCUMENTS

| | | |
|---|---|---|
| 868532 | 7/1978 | Belgium . |
| 12401 | 6/1980 | European Pat. Off. . |
| 45161 | 2/1982 | European Pat. Off. . |
| 0050800 | 5/1982 | European Pat. Off. ..... 260/112.5 R |
| 2027025 | 2/1980 | United Kingdom . |
| 2048863 | 12/1980 | United Kingdom . |

OTHER PUBLICATIONS

Almquist et al., "Synthesis and Biological Activity . . . Angiotensin Converting Enzyme", J. Med. Chem., 1980, 23, pp. 1392–1398.

Meyer et al., "Novel Synthesis of (S)-1-[5-(Benzoylamino)-1,4-dioxo-6-phenylhexyl]-L-proline", J. Med. Chem., 1981, 24, pp. 964–969.

Meyer et al., "Angiotensin Converting Enzyme Inhibitors: Modification of a Tripeptide Analogue, J. Med. Chem., 1982, 25, pp. 996–999.

Primary Examiner—Delbert R. Phillips
Attorney, Agent, or Firm—Lawrence S. Levinson; Stephen B. Davis

[57] ABSTRACT

Hydroxy substituted peptide compounds of the formula

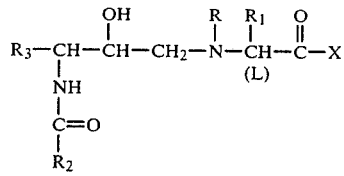

are disclosed. These compounds are useful as hypotensive agents due to their angiotensin converting enzyme inhibition activity and depending upon the definition of X may also be useful as analgesics due to their enkephalinase inhibition activity.

24 Claims, No Drawings

HYDROXY SUBSTITUTED PEPTIDE COMPOUNDS

BACKGROUND OF THE INVENTION

Meyer et al., "Angiotensin Converting Enzyme Inhibitors:Modifications Of A Tripeptide Analogue", J. Med. Chem., 1982, 25, 996-999, disclose the synthesis and angiotensin converting enzyme inhibition activity of compounds of the formula

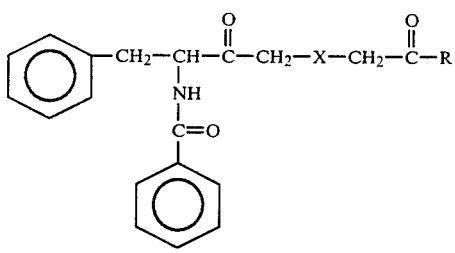

wherein X can be NH and R can be L-proline.

Almquist et al. in U.S. Pat. No. 4,329,473 disclose oxoalkanoic acid derivatives of L-proline as angiotensin converting enzyme inhibitors.

Gravestock et al. in European Patent Application No. 45161 disclose hypotensive compounds of the formula

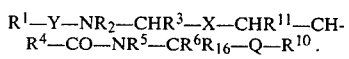

Mercaptoacyl derivatives of proline and substituted prolines are known to be useful hypotensive agents due to their angiotensin converting enzyme inhibition activity. Ondetti, et al. in U.S. Pat. No. 4,105,776 disclose such compounds wherein the proline ring is unsubstituted or substituted by an alkyl or hydroxy group. Ondetti, et al. in U.S. Pat. No. 4,154,935 disclose such compounds wherein the proline ring is substituted with one or more halogens. Ondetti, et al. in U.S. Pat. No. 4,316,906 disclose such compounds wherein the proline ring is substituted by various ethers and thioethers. Krapcho in U.S. Pat. No. 4,217,359 disclose such compounds wherein the proline ring has a carbamoyloxy substituent. Krapcho in U.S. Pat. No. 4,311,697 discloses compounds wherein the proline ring has a diether, dithioether, ketal or thioketal substituent in the 4-position. Krapcho in U.S. Pat. No. 4,316,905 discloses such compounds wherein the proline ring has a cycloalkyl, phenyl, or phenyl-lower alkylene substituent. Ondetti, et al. in U.S. Pat. No. 4,234,489 disclose such compounds wherein the proline has a keto substituent in the 5-position, Krapcho, et al. in U.S. Ser. No. 162,341 filed June 23, 1980, now U.S. Pat. No. 4,310,461, disclose such compounds wherein the proline has an imido, amido, or amino substituent in the 4-position. Iwao, et al. in U.K. Patent Application No. 2,027,025 disclose such compounds wherein the proline has an aromatic substituent in the 5-position.

Mercaptoacyl derivatives of 3,4-dehydroproline are disclosed as angiotensin converting enzyme inhibitors by Ondetti in U.S. Pat. No. 4,129,566. Mercaptoacyl derivatives of thiazolidinecarboxylic acid and substituted thiazolidinecarboxylic acid are disclosed as angiotensin converting enzyme inhibitors by Ondetti in U.S. Pat. No. 4,192,878 and by Yoshitomo Pharmaceutical Ind. in Belgium Patent No. 868,532.

Mercaptoacyl derivatives of dihydroisoindole carboxylic acids and tetrahydroisoquinoline carboxylic acids are disclosed as being useful hypotensive agents by Ondetti et al., in U.S. Ser. No. 69,031, filed Aug. 23, 1979. These mercaptoacyl tetrahydroisoquinoline compounds are also disclosed by Portlock in U.K. Application No. 2,048,863 and by Hayashi et al. in U.S. Pat. No. 4,256,751.

Rovnyak in U.S. Pat. Nos. 4,211,786, 4,254,267 and 4,266,065 discloses that mercaptoacyl and acylmercaptoacyl derivatives of 4-substituted or unsubstituted 1H-pyrazole-5-carboxylic acids possess angiotensin converting enzyme inhibition activity.

Ondetti et al. in U.S. Pat. Nos. 4,053,651 and 4,199,512 and Suh et al. in U.S. Pat. No. 4,256,761 disclose that mercaptoacyl and acylmercaptoacyl derivatives of various amino acids and N-substituted amino acids possess angiotensin converting enzyme inhibition activity.

Harris et al. in U.S. Pat. No. 4,374,829 dislose that various carboxyalkyl dipeptides possess angiotensin converting enzyme inhibition activity.

SUMMARY OF THE INVENTION

This invention is directed to hydroxy substituted peptide compounds of formula I and salts thereof

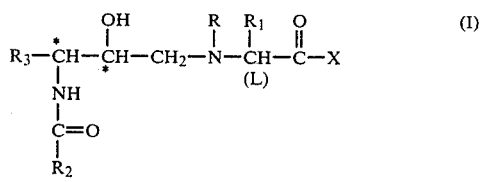

X is an amino or imino acid of the formula

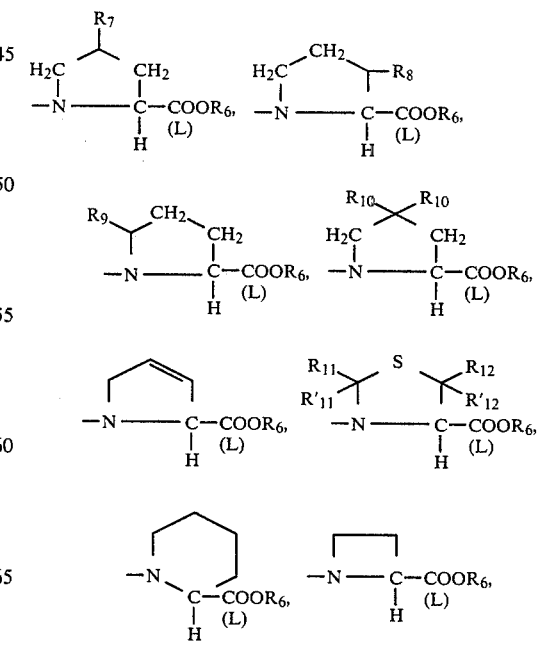

-continued

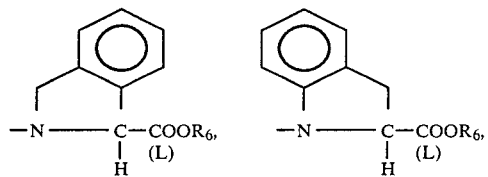

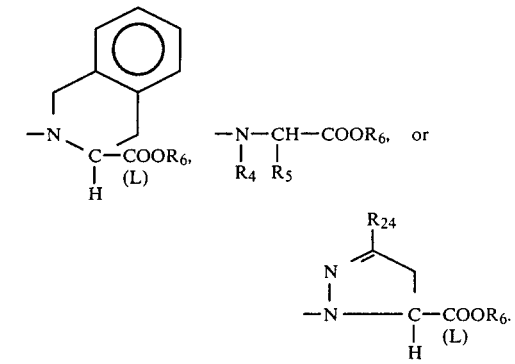

$R_7$ is hydrogen, lower alkyl, halogen, hydroxy

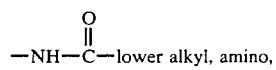

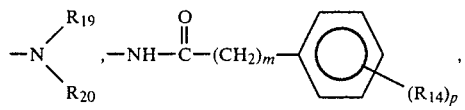

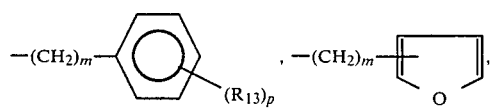

a 1- or 2-naphthyl of the formula

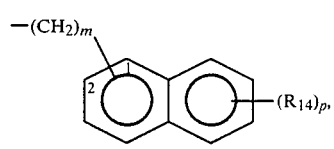

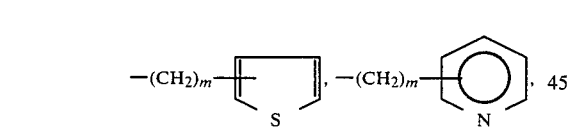

a 1- or 2-naphthyloxy of the formula

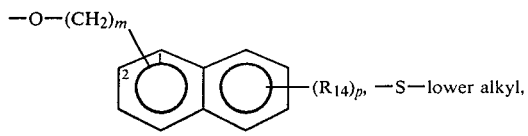

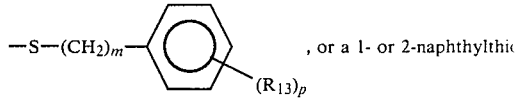

of the formula

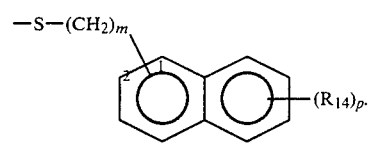

$R_8$ is halogen,

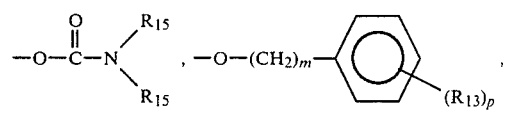

—O—lower alkyl, a 1- or 2-naphthyloxy of the formula

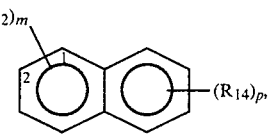

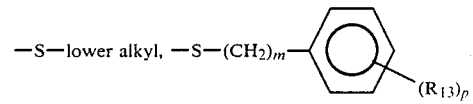

or a 1- or 2-naphthylthio of the formula

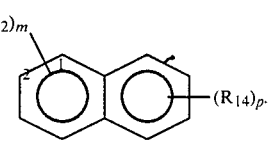

$R_9$ is keto or

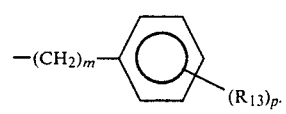

$R_{10}$ is halogen or —Y—$R_{16}$.
$R_{11}$, $R_{11}'$, $R_{12}$ and $R_{12}'$ are independently selected from hydrogen and lower alkyl or $R_{11}'$ $R_{12}$ and $R_{12}'$ are hydrogen and $R_{11}$ is

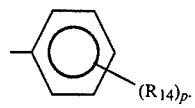

R₁₃ *l is hydrogen, lower alkyl of* 1 to 4 carbons, lower alkoxy of 1 to 4 carbons, lower alkylthio of 1 to 4 carbons, chloro, bromo, fluoro, trifluoromethyl, hydroxy, phenyl, phenoxy, phenylthio, or phenylmethyl.

R₁₄ is hydrogen, lower alkyl of 1 to 4 carbons, lower alkoxy of 1 to 4 carbons, lower alkylthio of 1 to 4 carbons, chloro, bromo, fluoro, trifluoromethyl, or hydroxy.

m is zero, one, two, three, or four.

p is one, two or three provided that p is more than one only if R₁₃ or R₁₄ is hydrogen, methyl, methoxy, chloro, or fluoro.

R₁₅ is hydrogen or lower alkyl of 1 to 4 carbons.

Y is oxygen or sulfur.

R₁₆ is lower alkyl of 1 to 4 carbons,

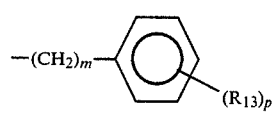

or the R₁₆ groups join to complete an unsubstituted 5- or 6-membered ring or said ring in which one or more of the carbons has a lower alkyl of 1 to 4 carbons or a di(lower alkyl of 1 to 4 carbons) substituent.

R₄ is hydrogen, lower alkyl,

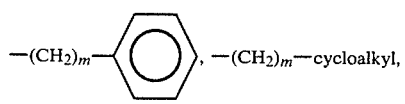

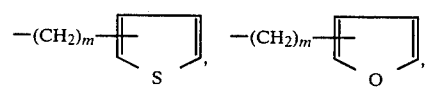

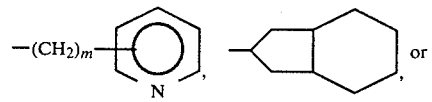

R₅ is hydrogen, lower alkyl,

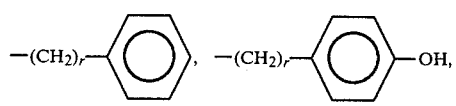

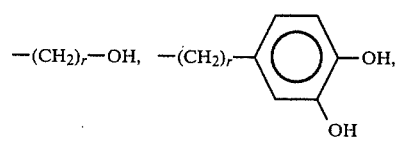

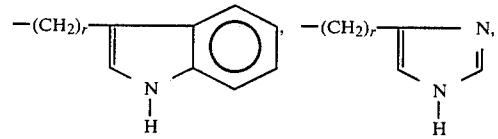

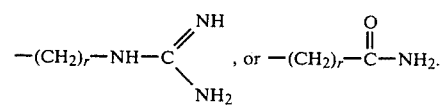

r is an integer from 1 to 4.

R₁₉ is lower alkyl, benzyl, or phenethyl.

R₂₀ is hydrogen, lower alkyl, benzyl or phenethyl.

R is hydrogen, lower alkyl, cycloalkyl,

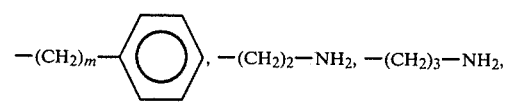

R₁ is hydrogen, lower alkyl, halo substituted lower alkyl,

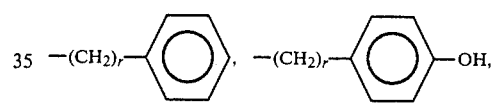

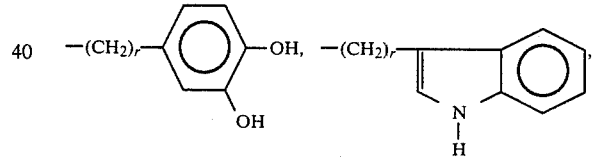

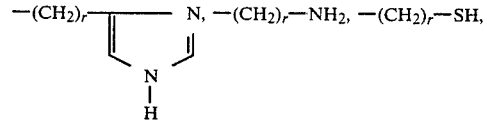

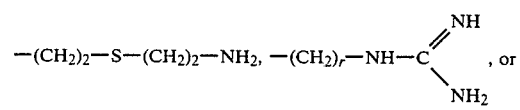

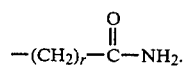

R₂ is

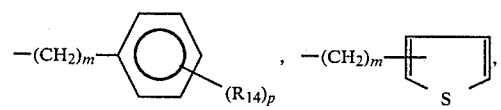

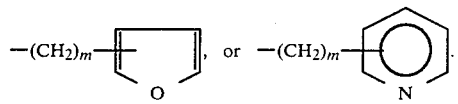

R₃ is hydrogen, lower alkyl,

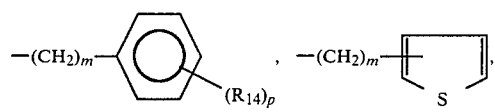

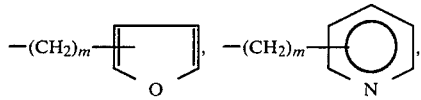

halo substituted lower alkyl, —(CH₂)ₘ—cycloalkyl,

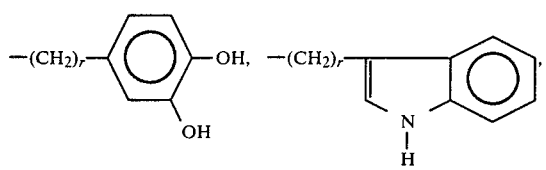

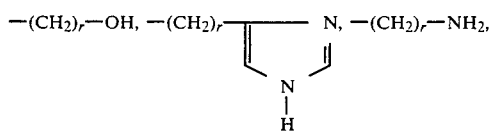

—(CH₂)ᵣ—SH, —(CH₂)ᵣ—S—lower alkyl,

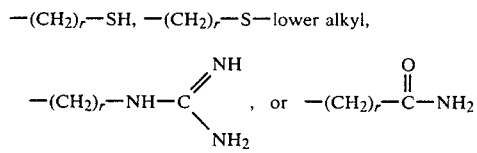

wherein m, $R_{14}$, p and r are as defined above.
$R_6$ is hydrogen, lower alkyl, benzyl, benzhydryl,

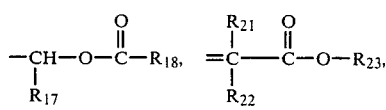

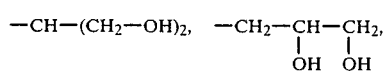

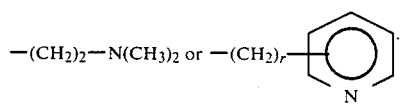

$R_{17}$ is hydrogen, lower alkyl, cycloalkyl, or phenyl.
$R_{18}$ is hydrogen, lower alkyl, lower alkoxy, or phenyl or $R_{17}$ and $R_{18}$ taken together are

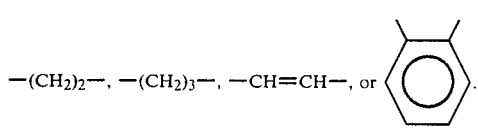

$R_{21}$ and $R_{22}$ are independently selected from hydrogen and lower alkyl.
$R_{23}$ is lower alkyl.
$R_{24}$ is hydrogen, lower alkyl,

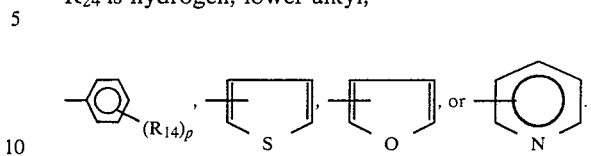

DETAILED DESCRIPTION OF THE INVENTION

This invention in its broadest aspects relates to the hydroxy substituted peptide compounds of formula I above, to compositions and the method of using such compounds as pharmaceutical agents.

The term lower alkyl used in defining various symbols refers to straight or branched chain radicals having up to seven carbons. The preferred lower alkyl groups are up to four carbons with methyl and ethyl most preferred. Similarly the terms lower alkoxy and lower alkylthio refer to such lower alkyl groups attached to an oxygen or sulfur.

The term cycloalkyl refers to saturated rings of 3 to 7 carbon atoms with cyclopentyl and cyclohexyl being most preferred.

The term halogen refers to chloro, bromo and fluoro.

The term halo substituted lower alkyl refers to such lower alkyl groups described above in which one or more hydrogens have been replaced by chloro, bromo or fluoro groups such as trifluoromethyl, which is preferred, pentafluoroethyl, 2,2,2-trichloroethyl, chloromethyl, bromomethyl, etc.

The symbols

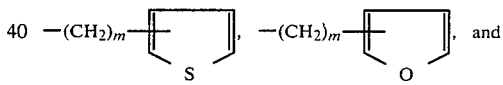

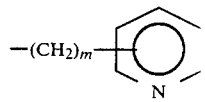

represent that the alkylene bridge is attached to an available carbon atom.

The compounds of formula I are obtained by treating a compound of the formula

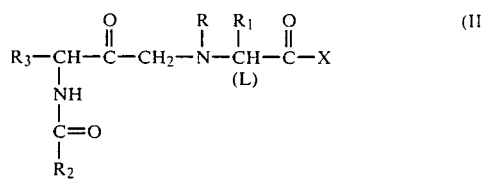

with a conventional reducing agent such as sodium borohydride, sodium cyanoborohydride, diisobutyl aluminum hydride, lithium tri t-butoxy aluminum hydride, etc.

The compounds of formula II can be prepared by various methods. For example, when R is hydrogen, a carboxymethyl peptide ester of the formula

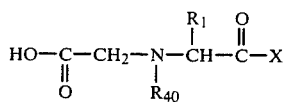 (III)

can be converted to its acid chloride and then reacted with an oxazolone of the formula

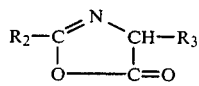 (IV)

wherein $R_{40}$ and $R_6$ (in the definition of X) are protecting groups such as, for example, wherein $R_{40}$ is benzyloxycarbonyl and $R_6$ is benzyl. Treatment with the reducing agent followed by removal of the $R_{40}$ and $R_6$ protecting groups, for example, by hydrogenation yields the product of formula I wherein $R_6$ is hydrogen.

The carboxymethyl peptide ester of formula III can be prepared by reacting the peptide ester of the formula

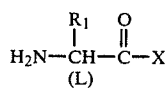 (V)

with tert-butyl bromoacetate and then introducing the $R_{40}$ protecting group, for example, by treating with benzyl chloroformate.

The compounds of formula II can also be prepared by reacting a ketone of the formula

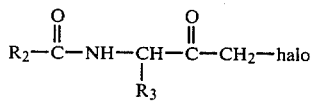 (VI)

wherein halo is Cl or Br with the peptide ester of the formula

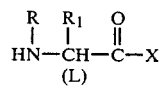 (VII)

in the presence of base such as sodium bicarbonate. Treatment with the reducing agent followed by removal of the $R_6$ ester group yields the product of formula I wherein $R_6$ is hydrogen.

The ketone intermediate of formula VI can be prepared by treating a ketone of the formula

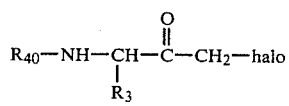 (VIII)

wherein $R_{40}$ is a protecting group such as benzyloxycarbonyl with hydrogen bromide and acetic acid followed by reaction with the acid halide of the formula

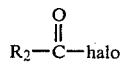 (IX)

in the presence of base such as sodium bicarbonate.

The compounds of formula II can also be prepared by reacting an aminoketone of the formula

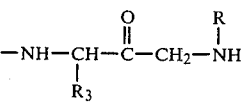 (X)

particularly the hydrochloride salt thereof with the haloacetyl amino or imino acid ester of the formula

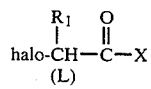 (XI)

wherein $R_6$ in the definition of X is an easily removable ester protecting group and halo is Cl or Br.

The compounds of formula II can also be prepared by coupling an aminoketone carboxylic acid or its chemical equivalent of the formula

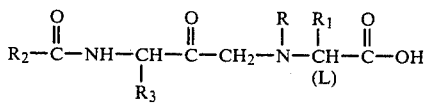 (XII)

with the amino or imino acid or ester of the formula

HX.   (XIII)

This reaction can be performed in the presence of a coupling agent such as dicyclohexylcarbodiimide or the like, or by conversion of the acid of formula XII to its mixed anhydride, symmetrical anhydride, acid halide, active ester or by use of Woodward reagent K, N-ethoxycarbonyl-2-ethoxy-1,2-dihydroquinoline or the like. For a review of the methods of acylation see Methoden der Organischen Chemie (Houben-Weyl), Vol. XV, part II, page 1 et seq. (1974). Preferably, the N-hydroxysuccinimide active ester form of the compound of formula XII is reacted with the acid of formula XIII.

In these reactions, if R is hydrogen then that N-atom can be protected by an easily removable protecting group such as benzyloxycarbonyl.

The aminoketone of formula X can be prepared by converting the carboxyalkylamine of the formula

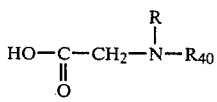 (XIV)

wherein $R_{40}$ is a protecting group such as benzyloxycarbonyl, to its acid chloride and then reacting with an oxazolone of formula IV to yield

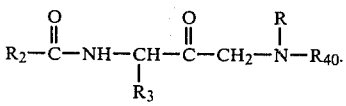 (XV)

Removal of the $R_{40}$ protecting group such as by hydrogenation yields the reactant of formula X.

The aminoketone of formula X wherein R is other than hydrogen can also be prepared by reacting the ketone of formula VI with a substituted amine of the formula

The aminoketone carboxylic acid of formula XII can be prepared by reacting the aminoketone of formula X with a haloacetic acid ester of the formula

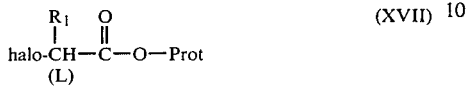

wherein Prot is an easily removable ester protecting group such as t-butyl to yield the ester

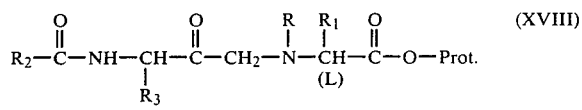

Removal of the ester protecting group gives the reactant of formula XII.

In the above reactions if any or all of R, $R_1$, $R_3$ and $R_5$ are

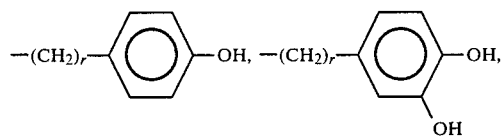

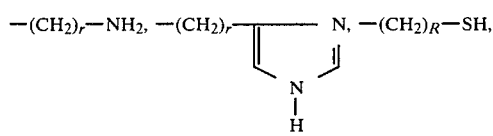

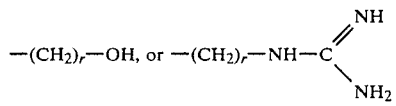

then the hydroxyl, amino, imidazolyl, mercaptan or guanidinyl function should be protected during the reaction. Suitable protecting groups include benzyloxycarbonyl, t-butoxycarbonyl, benzyl, benzhydryl, trityl, etc., and nitro in the case of guanidinyl. The protecting group is removed by hydrogenation, treatment with acid, or other known methods following completion of the reaction.

The ester products of formula I wherein $R_6$ is lower alkyl, benzyl or benzhydryl can be chemically treated such as with sodium hydroxide in aqueous dioxane or with trifluoroacetic acid to yield the products of formula I wherein $R_6$ is hydrogen. The benzyl and benzhydryl esters can also be hydrogenated, for example, by treating with hydrogen in the presence of a palladium on carbon catalyst.

The ester products of formula I wherein $R_6$ is

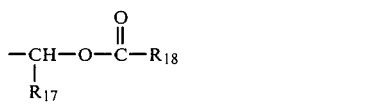

may be obtained by employing the peptide of formula V or VII or the haloacetyl amino or imino acid ester of formula XI in the above reactions with such ester group already in place. Such ester reactants can be prepared by treating the peptide of formula V or VII or the haloacetyl amino or imino acid ester of formula XI wherein $R_6$ is hydrogen with an acid chloride such as

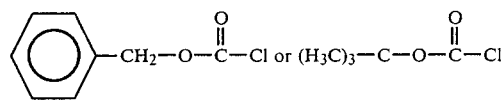

so as to protect the N-atom. The protected compound is then reacted in the presence of a base with a compound of the formula

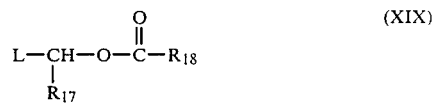

wherein L is a leaving group such as chlorine, bromine, tolylsulfonyl, etc., followed by removal of the N-protecting group such as by treatment with acid or hydrogenation.

The ester products of formula I wherein $R_6$ is

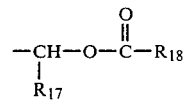

can also be obtained by treating the product of formula I wherein $R_6$ is hydrogen with a molar excess of the compound of formula XIX.

The ester products of formula I wherein $R_6$ is

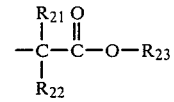

can be prepared by treating the product of formula I wherein $R_6$ is hydrogen with a molar excess of the compound of the formula

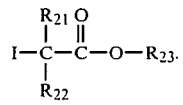

The ester products of formula I wherein $R_6$ is

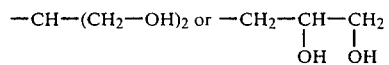

can be prepared by coupling the product of formula I wherein $R_6$ is hydrogen with a molar excess of the compound of the formula

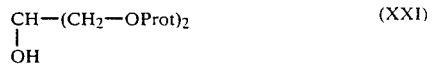

or the formula

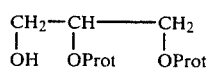 (XXII)

in the presence of a coupling agent such as dicyclohexylcarbodiimide followed by removal of the hydroxyl protecting groups.

Similarly, the ester products of formula I wherein $R_6$ is

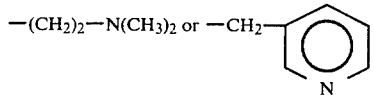

can can be prepared by coupling the product of formula I wherein $R_6$ is hydrogen with a molar excess of the compound of the formula

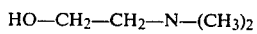 (XXIII)

or the formula

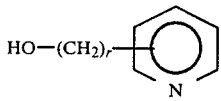 (XXIV)

in the presence of a coupling agent such as dicyclohexylcarbodiimide.

The esters of formula I wherein $R_6$ is lower alkyl can be obtained from the carboxylic acid compounds, i.e., wherein $R_6$ is hydrogen, by conventional esterification procedures, e.g., treatment with an alkyl halide of the formula $R_6$—halo or an alcohol of the formula $R_6$—OH.

The peptide esters of formulas V and VII may be obtained by coupling the hydrochloride salt of the amino or imino acid ester of formula XIII wherein $R_6$ is, for example, benzyl with the N-protected amino acid of the formula

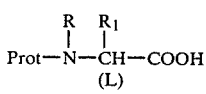 (XXV)

wherein Prot is a protecting group such as

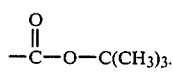

Preferably, this reaction is performed in the presence of a coupling agent such as dicyclohexylcarbodiimide. Removal of the N-protecting group, for example, by treatment with trifluoroacetic acid yields the peptide esters of formulas V and VII.

The products of formula I wherein $R_7$ is amino may be obtained by reducing the corresponding products of formula I wherein $R_7$ is azido.

Preferred compounds of this invention with respect to the peptide part of the structure of formula I are those wherein:

R is hydrogen or straight or branched chain lower alkyl of 1 to 4 carbons.

$R_1$ is hydrogen, straight or branched chain lower alkyl or 1 to 4 carbons, —$CF_3$, —$(CH_2)_r$—$NH_2$ wherein r is an integer from 1 to 4,

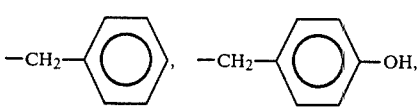

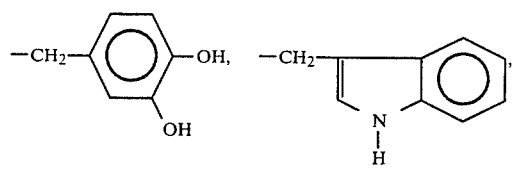

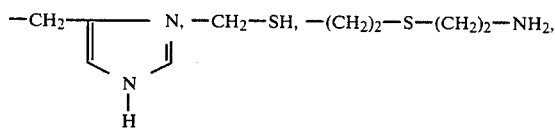

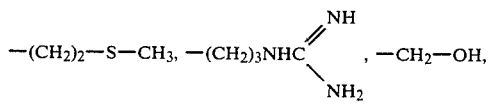

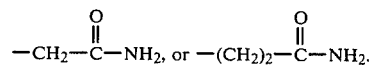

$R_4$ is hydrogen, cyclohexyl or phenyl.
$R_5$ is hydrogen, straight or branched chain lower alkyl of 1 to 4 carbons,

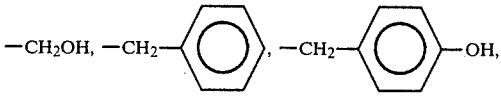

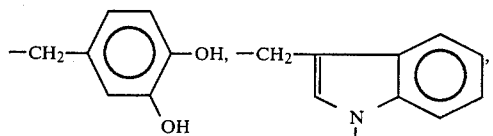

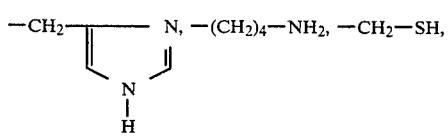

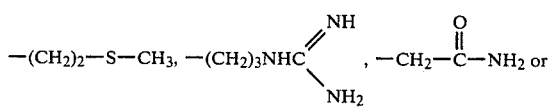

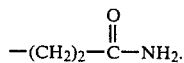

$R_6$ is hydrogen, straight or branched chain lower alkyl of 1 to 4 carbons, alkali metal salt,

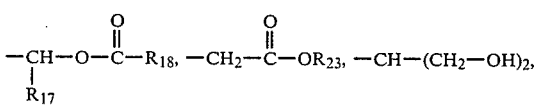

-continued

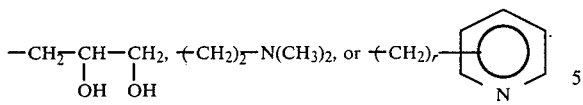

r is an integer from 1 to 4.

$R_{23}$ is straight or branched chain lower alkyl of 1 to 4 carbons, especially —C(CH₃)₃.

$R_{17}$ is hydrogen, straight or branched chain lower alkyl of 1 to 4 carbons, or cyclohexyl.

$R_{18}$ is straight or branched chain lower alkyl of 1 to 4 carbons or phenyl.

$R_7$ is hydrogen.

$R_7$ is hydroxy.

$R_7$ is straight or branched chain lower alkyl of 1 to 4 carbons or cyclohexyl.

$R_7$ is amino.

$R_7$ is —O—lower alkyl wherein lower alkyl is straight or branched chain of 1 to 4 carbons.

$R_7$ is

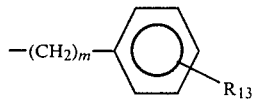

wherein m is zero, one or two and $R_{13}$ is hydrogen, methyl, methoxy, methylthio, chloro, bromo, fluoro, or hydroxy.

$R_7$ is

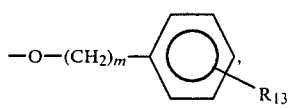

1-naphthyloxy or 2-naphthyloxy wherein m is zero, one, or two and $R_{13}$ is hydrogen, methyl, methoxy, methylthio, chloro, bromo, fluoro, or hydroxy.

$R_7$ is —S—lower alkyl wherein lower alkyl is straight or branched chain of 1 to 4 carbons.

$R_7$ is

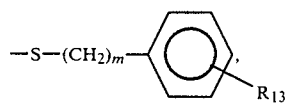

1-naphthylthio, or 2-naphthylthio wherein m is zero, one, or two and $R_{13}$ is hydrogen, methyl, methoxy, methylthio, chloro, bromo, fluoro, or hydroxy.

$R_8$ is —O—lower alkyl wherein lower alkyl is straight or branched chain of 1 to 4 carbons.

$R_8$ is

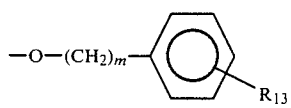

wherein m is zero, one, or two and $R_{13}$ is hydrogen, methyl, methoxy, methylthio, chloro, bromo, fluoro, or hydroxy.

$R_8$ is —S—lower alkyl wherein lower alkyl is straight or branched chain of 1 to 4 carbons.

$R_8$ is

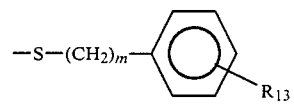

wherein m is zero, one or two and $R_{13}$ is hydrogen, methyl, methoxy, methylthio, chloro, bromo, fluoro or hydroxy.

$R_9$ is phenyl, 2-hydroxyphenyl, or 4-hydroxyphenyl.

$R_{10}$ are both fluoro or chloro.

$R_{10}$ are both —Y—$R_{16}$ wherein Y is O or S, $R_{16}$ is straight or branched chain lower alkyl of 1 to 4 carbons or the $R_{16}$ groups join to complete an unsubstituted 5- or 6-membered ring or said ring in which one or more of the available carbons has a methyl or dimethyl substituent.

$R_{11}$, $R_{11}'$, $R_{12}$ and $R_{12}'$ are all hydrogen, or $R_{11}$ is phenyl, 2-hydroxyphenyl, or 4-hydroxyphenyl and $R_{11}'$, $R_{12}$ and $R_{12}'$ are hydrogen.

$R_{24}$ is phenyl.

Most preferred compounds of this invention with respect to the peptide part of the structure of formula I are those wherein:

X is

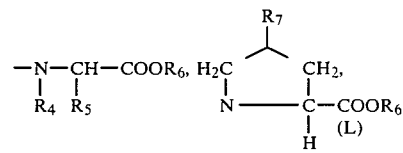

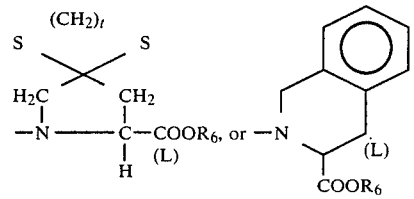

R is hydrogen or methyl.

$R_1$ is hydrogen, methyl, or —(CH₂)—₄NH₂.

$R_6$ is hydrogen, straight or branched chain lower alkyl of 1 to 4 carbons, or an alkali metal salt.

$R_4$ is cyclohexyl or phenyl and $R_5$ is hydrogen.

$R_4$ is hydrogen and $R_5$ is methyl,

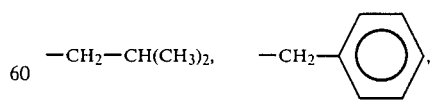

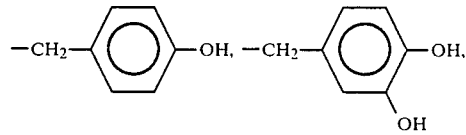

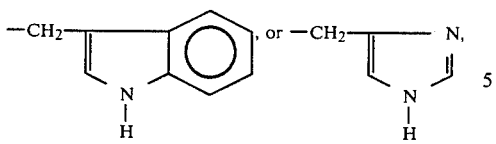

$R_7$ is hydrogen, cyclohexyl, lower alkoxy of 1 to 4 carbons,

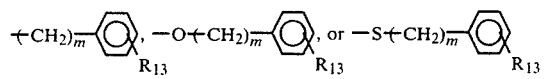

wherein m is zero, one, or two and $R_{13}$ is hydrogen, methyl, methoxy, methylthio, Cl, Br, F, or hydroxy, especially preferred wherein $R_7$ is hydrogen.

t is two or three, especially where t is two.

Preferred compounds of this invention with respect to the hydroxy substituted portion of the structure of formula I are those wherein:

$R_2$ is

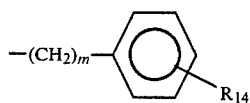

wherein m is zero, one, or two and $R_{14}$ is hydrogen, methyl, methoxy, methylthio, Cl, Br, F, or hydroxy, especially phenyl.

$R_3$ is straight or branched chain lower alkyl of 1 to 4 carbons, —(CH$_2$)$_r$—NH$_2$,

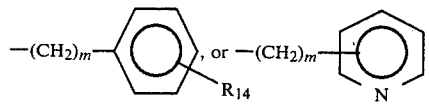

wherein m is zero, one, or two, $R_{14}$ is hydrogen, methyl, methoxy, methylthio, Cl, Br, F, or hydroxy, and r is an integer from 1 to 4, especially benzyl or methyl.

The compounds of formula I wherein $R_6$ is hydrogen form salts with a variety of inorganic or organic bases. The nontoxic, pharmaceutically acceptable salts are preferred, although other salts are also useful in isolating or purifying the product. Such pharmaceutically acceptable salts include metal salts such as sodium, potassium or lithium, alkaline earth metal salts such as calcium or magnesium, and salts derived from amino acids such as arginine, lysine, etc. The salts are obtained by reacting the acid form of the compound with an equivalent of the base supplying the desired ion in a medium in which the salt precipitates or in aqueous medium and then lyophilizing.

Similarly, the compounds of formula I form salts with a variety of inorganic and organic acids. Again, the non-toxic pharmaceutically acceptable salts are preferred, although other salts are also useful in isolating or purifying the product. Such pharmaceutically acceptable salts include those formed with hydrochloric acid, methanesulfonic acid, sulfuric acid, maleic acid, etc. The salts are obtained by reacting the product with an equivalent amount of the acid in a medium in which the salt precipitates.

As shown above, the peptide portion of the molecule of the products of formula I represented by

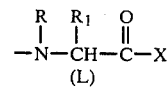

is in the L-configuration ($R_1$ is other than hydrogen). One or two asymmetric centers are also present in the hydroxy substituted portion of the molecule as represented by the * in formula I. Of course, if $R_3$ is hydrogen, then only one center is present. Thus, the compounds of formula I can exist in diastereoisometric forms or in mixtures thereof. The above described processes can utilize racemates, enantiomers or diastereomers as starting materials. When diastereomeric products are prepared, they can be separated by conventional chromatographic or fractional crystallization methods.

The products of formula I wherein the imino acid ring is monosubstituted give rise to cis-trans isomerism. The configuration of the final product will depend upon the configuration of the $R_7$, $R_8$ and $R_9$ substituent in the starting material of formula XII.

The compounds of formula I, and the pharmaceutically acceptable salts thereof, are hypotensive agents. They inhibit the conversion of the decapeptide angiotensin I to angiotensin II and, therefore, are useful in reducing or relieving angiotensin related hypertension. The action of the enzyme renin on angiotensinogen, a pseudoglubulin in blood, produces angiotensin I. Angiotensin I is converted by angiotensin converting enzyme (ACE) to angiotensin II. The latter is an active pressor substance which has been implicated as the causative agent in several forms of hypertension in various mammalian species, e.g., humans. The compounds of this invention intervene in the angiotensinogen→(renin)→angiotensin I→angiotensin II sequence by inhibiting angiotensin converting enzyme and reducing or eliminating the formation of the pressor substance angiotensin II. Thus by the administration of a composition containing one (or a combination) of the compounds of this invention, angiotensin dependent hypertension in a species of mammal (e.g., humans) suffering therefrom is alleviated. A single dose, or preferably two to four divided daily doses, provided on a basis of about 0.1 to 100 mg., preferably about 1 to 50 mg., per kg. of body weight per day is appropriate to reduce blood pressure. The substance is preferably administered orally, but parenteral routes such as the subcutaneous, intramuscular, intravenous or intraperitoneal routes can also be employed.

The compounds of this invention can also be formulated in combination with a diuretic for the treatment of hypertension. A combination product comprising a compound of this invention and a diuretic can be administered in an effective amount which comprises a total daily dosage of about 30 to 600 mg., preferably about 30 to 330 mg. of a compound of this invention, and about 15 to 300 mg., preferably about 15 to 200 mg. of the diuretic, to a mammalian species in need thereof. Exemplary of the diuretics contemplated for use in combination with a compound of this invention are the thiazide diuretics, e.g., chlorothiazide, hydrochlorothiazide, flumethiazide, hydroflumethiazide, bendroflumethiazide, methyclothiazide, trichloromethiazide, polythiazide or benzthiazide as well as ethacrynic acid, ticrynafen, chlorthalidone, furosemide, musolimine, bumetanide, triamterene, amiloride and spironolactone and salts of such compounds.

The compounds of formula I can be formulated for use in the reduction of blood pressure in compositions such as tablets, capsules or elixirs for oral administration, or in sterile solutions or suspensions for parenteral administration. About 10 to 500 mg. of a compound of formula I is compounded with physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

The compounds of formula I wherein X is

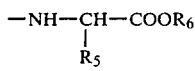

also possess enkephalinase inhibition activity and are useful as analgesic agents. Thus, by the administration of a composition containing one or a combination of such compounds of formula I or a pharmaceutically acceptable salt thereof, pain is alleviated in the mammalian host. A single dose, or preferably two to four divided daily doses, provided on a basis of about 0.1 to about 100 mg. per kilogram of body weight per day, preferably about 1 to about 50 mg. per kilogram per day, produces the desired analgesic activity. The composition is preferably administered orally but parenteral routes such as subcutaneous can also be employed.

The following examples are illustrative of the invention. Temperatures are given in degrees centigrade. LH-20 refers to a Sephadex chromatography gel commercially available from Pharmacia Fine Chemicals.

EXAMPLE 1

(3S)-1-[N-[3-(Benzoylamino)-2-hydroxy-4-phenylbutyl]-L-alanyl]-L-proline, monohydrochloride (a) (S)-3-Amino-1-chloro-4-phenyl-2-butanone, hydrogen bromide (S)-[3-Chloro-2-oxo-1-(phenylmethyl)propyl]carbamic acid, phenylmethyl ester (51.4 g.) is dissolved in a mixture of acetic acid (252 ml.) and hydrogen bromide in acetic acid (3.45N, 348 ml.) and kept at room temperature for 1.5 hours. The reaction mixture is then concentrated in vacuo and precipitated with ether to obtain 36.6 g. of (S)-3-amino-1-chloro-4-phenyl-2-butanone, hydrogen bromide; m.p. (175°) 177°-179°.

(b) (S)-N-[3-Chloro-2-oxo-1-(phenylmethyl)propyl]benzamide (S)-3-Amino-1-chloro-4-phenyl-2-butanone, hydrogen bromide (36.3 g., 130.3 mmole) is suspended in 520 ml. of dry tetrahydrofuran and 18.2 ml. of triethylamine (130.3 mmole) with stirring for ten minutes. The mixture is placed in an ice bath and 15.2 ml. of benzoyl chloride is added followed by 10.95 g. of sodium bicarbonate. After 5 minutes the ice bath is removed and the reaction mixture is kept at room temperature for 1.5 hours. The reaction mixture is then concentrated in vacuo and the residue taken up in 1 l. of aqueous methanol (10% water). The precipitate is collected, filtered and washed with methanol to obtain 25.3 g. of (S)-N-[3-chloro-2-oxo-1-(phenylmethyl)propyl]benzamide; m.p (160°) 170°-172° (dec.); $[\alpha]_D^{23} = -129°$ (c=1.7, dimethylformamide).

(c) (S)-N-[3-(Benzoylamino)-2-oxo-4-phenylbutyl]-L-alanine, 1,1-dimethylethyl ester A mixture of (S)-N-[3-chloro-2-oxo-1-(phenylmethyl)propyl]benzamide (2.0 g., 6.62 mmole), L-alanine. 1,1-dimethylethyl ester (1.2 g., 6.60 mmole), sodium bicarbonate (1.2 g., 14.28 mmole) and sodium iodide (1.0 g., 6.67 mmole) in dry dimethylformamide (15 ml.) at room temperature is stirred under argon. After stirring for 19 hours, the resulting mixture is diluted with ether and washed with water (twice) and 1N sodium bicarbonate. The organic layer is then extracted with 1N hydrochloric acid (6×25 ml.). The hydrochloric acid fractions are combined and back extracted with hexane and the organic layers are discarded. The hydrochloric acid fraction is then basified with sodium bicarbonate (20 g.) and extracted with ethyl acetate (2×150 ml.). The ethyl acetate fractions are combined and washed with water and brine. After drying (MgSO$_4$), the solvent is removed at reduced pressure to give 1.24 g. of (S)-N-[3-(benzoylamino)-2-oxo-4-phenylbutyl]-L-alanine, 1,1-dimethylethyl ester as a light yellow solid. This material is combined with that from a previous run and the product is recrystallized from ether/ethyl acetate to give the desired product as a nearly colorless solid, m.p. 109°-111°; $[\alpha]_D^{20} = +34.9°$ (c=2, chloroform). R$_f$ 0.41 (silica gel, ethyl acetate).

Anal. Calc'd. for $C_{24}H_{30}N_2O_4$: C, 70.22; H, 7.37; N, 6.82. Found: C, 70.02; H, 7.23; N, 6.76.

(d) (S)-N-[N-(Benzoylamino)-2-oxo-4-phenylbutyl]-N-[(phenylmethoxy)carbonyl]-L-alanine, 1,1-dimethylethyl ester To a solution of the ester product from part (c) (2.85 g., 6.94 mmole) in dry benzene (55 ml.) under argon is added pyridine (2.80 ml., 5 eq.) followed by benzyl chloroformate (1.98 ml., 2 eq.) After stirring for 2 hours, the mixture is diluted with ether and the resulting solution is washed with 1N hydrochloric acid (twice), 1N sodium bicarbonate (twice), and brine. After drying (MgSO$_4$), the solvent is removed at reduced pressure and the residue is flash chromatographed (silica gel LPS-1; hexane/acetone; 4:1) to give 3.41 g. of (S)-N-[N-(benzoylamino)-2-oxo-4-phenylbutyl]-N-[(phenylmethoxy)carbonyl]-L-alanine, 1,1-dimethylethyl ester as a colorless foam. R$_f$ 0.30 (silica gel, hexane/acetone; 7:3).

(e) (S)-N-[N-(Benzoylamino)-2-oxo-4-phenylbutyl]-N-[(phenylmethoxy)carbonyl]-L-alanine To a solution of the ester product from part (d) (3.41 g., 6.26 mmole) in dry dichloromethane (35 ml.) is added trifluoroacetic acid (20 ml.). After stirring at room temperature for 20 minutes, the solvent is removed at reduced pressure and chased three times with toluene. The resulting residue is dissolved in ether (100 ml.) and washed with water, 1N hydrochloric acid, and water. The ether fraction is then extracted with 0.4N sodium bicarbonate (2×100 ml.). The aqueous fractions are combined and backwashed with ether and the ether fractions are discarded. The aqueous fraction is then acidified with 1N hydrochloric acid and extracted with ethyl acetate (2×250 ml.). The ethyl acetate fractions are combined and washed with water and brine. After drying (MgSO₄), the solvent is removed at reduced pressure to give 2.97 g. of (S)-N-[N-(benzoylamino)-2-oxo-4-phenylbutyl]-N-[(phenylmethoxy)carbonyl]-L-alanine as a colorless foamy solid. R$_f$ 0.46 (silica gel; ethyl acetate:pyridine:acetic acid:water; 350:20:6:11).

(f)
(S)-1-[N-[3-(Benzoylamino)-2-oxo-4-phenylbutyl]-N-[(phenylmethoxy)carbonyl]-L-alanyl]-L-proline, phenylmethyl ester To a solution of the acid product from part (e) (0.5 g., 1.02 mmole), 1-hydroxybenzotriazole hydrate (0.14 g., 1.02 eq.) in dry tetrahydrofuran (4 ml.) under argon is added 2-morpholinoethyl isocyanide (0.17 ml., 1.2 eq.). The resulting mixture is stirred at room temperature for one hour, after which, L-proline, phenylmethyl ester, hydrochloride (0.25 g., 1.02 eq.) is added followed by diisopropylethylamine (0.18 ml., 1 eq.). After stirring for 18 hours, the mixture is diluted with ethyl acetate and the resulting solution is washed with 1N hydrochloric acid (twice), 0.5N sodium bicarbonate, and brine. After drying (MgSO₄), the solvent is removed at reduced pressure and the residue is flash chromatographed (silica gel LPS-1; hexane:ethyl acetate; 1:1) to give 0.56 g. of (S)-1-[N-[3-(benzoylamino)-2-oxo-4-phenylbutyl]-N-[(phenylmethoxy)carbonyl]-L-alanyl]-L-proline, phenylmethyl ester as a colorless oil. R$_f$ 0.41 (silica gel; benzene:acetone; 4:1).

(g)
(3S)-1-[N-[3-(Benzoylamino)-2-hydroxy-4-phenylbutyl]-N-[(phenylmethoxy)carbonyl]-L-alanyl]-L-proline, phenylmethyl ester To a solution of the ester product from part (f) (0.51 g., 0.76 mmole) in tetrahydrofuran (20 ml.) and water (5 ml.) at 0° is added sodium borohydride (86 mg., 2.27 mmole). After stirring for 3 hours at 0°, the reaction is quenched with 1N hydrochloric acid and extracted with ether. The ether fraction is then washed with 1N hydrochloric acid, 1N sodium bicarbonate, and brine. After drying (MgSO₄), the solvent is removed at reduced pressure to give a colorless oil. This material is combined with that from a smaller run (0.10 g.) and flash chromatographed (silica gel LPS-1; hexane:ethyl acetate; 45:55) to give 0.57 g. of (3S)-1-[N-[3-(benzoylamino)-2-hydroxy-4-phenylbutyl]-N-[(phenylmethoxy)carbonyl]-L-alanyl]-L-proline, phenylmethyl ester as a colorless oil. R$_f$ 0.18 (silica gel, hexane:ethyl acetate; 35:65).

(h)
(3S)-1-[N-[3-(Benzoylamino)-2-hydroxy-4-phenylbutyl]-L-alanyl]-L-proline, monohydrochloride A mixture of the ester product from part (g) (0.57 g., 0.84 mmole), 2.0 ml. of 1N hydrochloric acid, absolute ethanol (30 ml.), and 10% palladium on carbon catalyst (200 mg.) is stirred under a hydrogen atmosphere. After stirring for 4 hours, the resulting mixture is filtered (millipore) and the filtrate concentrated at reduced pressure to give a colorless oil, which upon the addition of ether, gives a gummy solid. The solvent is removed at reduced pressure and the residue is dried under vacuum to give 0.31 g. of (3S)-1-[N-[3-(benzoylamino)-2-hydroxy-4-phenylbutyl]-L-alanyl]-L-proline, monohydrochloride as a colorless solid; m.p. 155°–165°; $[\alpha]_D^{20} = -94°$ (c=1.12, methanol). R$_f$ 0.44, 0.55 (trace) (silica gel; n-butanol:acetic acid:water; 4:1:1).

Anal. calc'd. for $C_{25}H_{31}N_3O_5 \cdot HCl \cdot H_2O$: C, 59,10; H, 6.74; N, 8.27; Cl, 6.98. Found: C, 58.95; H, 6.59; N, 8.03; Cl, 7.26.

EXAMPLE 2

(4S)-[[[3-(Benzoylamino)-2-hydroxy-4-phenylbutyl]methylamino]acetyl]-4-(phenylthio)-L-proline, monohydrochloride (a) (4S)-1-(Bromoacetyl)-4-(phenylthio)-L-proline To a suspension of (4S)-4-(phenylthio)-L-proline (2.2 g., 10 mmole) in methylene chloride (50 ml., freshly distilled) is added bis(trimethylsilyl) acetamide (7.35 ml., 30 mmole). The reaction mixture is stirred at room temperature for 2 hours until it becomes almost clear. The reaction mixture is then cooled to −5° and bromoacetyl chloride (1.9 g., 1.0 ml., 12 mmole) is added dropwise keeping the temperature at −5°. After stirring overnight (−5° to room temperature), the reaction mixture is concentrated to about 50% of its volume, partitioned between saturated sodium bicarbonate/ethyl acetate and the layers are separated. The organic layer is extracted once more with saturated sodium bicarbonate. The combined aqueous layers are acidified to pH 2.0 with 10% potassium bisulfate and extracted with ethyl acetate (3x). The ethyl acetate fractions are combined, dried (Na₂SO₄) and concentrated to give 3.5 g. of (4S)-1-(bromoacetyl)-4-(phenylthio)-L-proline as a viscous oil.

(b) (4S)-1-(Bromoacetyl)-4-(phenylthio)-L-proline, diphenylmethyl ester

A solution of diphenyldiazomethane (2.0 g., 10.2 mmole) in ethyl acetate (50 ml.) is added dropwise to a solution of (4S)-1-(bromoacetyl)-4-(phenylthio)-L-proline (3.5 g., 10.2 mmole) in ethyl acetate (50 ml.). The purple solution is stirred at room temperature overnight. The decolorized reaction mixture is washed with saturated sodium carbonate (twice) and water (twice), dried (Na₂SO₄), and concentrated to give 4.78 g. of (4S)-1-(bromoacetyl)-4-(phenylthio)-L-proline, diphenylmethyl ester as a yellow viscous oil.

(c)
[3-(Benzoylamino)-2-oxo-4-phenylbutyl]methylcarbamic acid, phenylmethyl ester N-methyl-N-[(phenylmethoxy)carbonyl]glycine (2.23 g., 10 mmole) is dissolved in 30 ml. of tetrahydrofuran and cooled in an ice-bath. Oxalyl chloride (1 ml., 11.5 mmole) is added followed by 2 drops of dimethylformamide. After stirring for 30 minutes in the ice-bath, the mixture is then stirred at room temperature for an hour. To this 0.25 ml. of oxalyl chloride is added. The mixture is evaporated, redissolved in 15 ml. of tetrahydrofuran, and stirred in an ice bath. A solution of 2-phenyl-4-(phenylmethyl)-5(4H)-oxazolone (3.1 g., 12.4 mmole) dissolved in 15 ml. of tetrahydrofuran is added to the above solution stirring in the ice-bath. Triethylamine (1.4 ml., 10 mmole) is added and the solution is stirred at room temperature overnight. The precipitated triethylamine hydrochloride salt is filtered off. Tetrahydrofuran is removed from the residue and it is then redissolved in pyridine (5 ml.) and 4-dimethylamino pyridine (20 mg.) is added. After stirring at room temperature for 3 hours, acetic acid (5 ml.) is added and the reaction mixture is kept at 105° for 30 minutes. The reaction mixture is then evaporated, the residue is dissolved in ethyl acetate, and washed with aqueous sodium bicarbonate and water. After trituration with ethyl acetate/hexane, 2.2 g. of homogeneous [3-(benzoylamino)-2-oxo-4-phenylbutyl]methylcarbamic acid, phenylmethyl ester is obtained; m.p. 140°–141°.

(d)

(±)-N-[3-(Methylamino)-2-oxo-1-(phenylmethyl)-propyl]benzamide, hydrochloride

[3-(Benzoylamino)-2-oxo-4-phenylbutyl]methylcarbamic acid, phenylmethyl ester (0.5 g.) is dissolved in ethanol (50 ml.) containing 1N hydrochloric acid (2 ml.). Palladium carbon catalyst (10%, 100 mg.) is added and hydrogenation is continued overnight. The reaction mixture is then filtered, evaporated, dissolved in water, and lyophilized to 300 mg. of (±)-N-[3-(methylamino)-2-oxo-1-(phenylmethyl)propyl]benzamide, hydrochloride as a homogeneous white powder.

(e)

[1(±),4S]-1-[[[3-(Benzoylamino)-2-oxo-4-phenylbutyl]methylamino]acetyl]-4-(phenylthio)-L-proline, diphenylmethyl ester To a solution of (4S)-1-(bromoacetyl)-4-(phenylthio)-L-proline, diphenylmethyl ester (4.78 g., 9.4 mmole) in dimethylformamide (20 ml.) is added (±)-N-[3-(methylamino)-2-oxo-1-(phenylmethyl)propyl]benzamide, hydrochloride (2.42 g., 7.2 mmole), and diisopropylethylamine (0.93 g., 1.25 ml., 7.2 mmole). After stirring overnight at room temperature, the reaction mixture is poured into water (50 ml.) and extracted with ethyl acetate (3x). The combined ethyl acetate extracts are washed with saturated sodium bicarbonate (twice) and water (twice), dried (Na2SO4), and concentrated into a yellow oil (6.2 g.). Flash chromatography (Merck silica gel, 2% methanol/methylene chloride) gives 3.2 g. of [1(±),4S]-1-[[[3-(benzoylamino)-2-oxo-4-phenylbutyl]methylamino]acetyl]-4-(phenylthio)-L-proline, diphenylmethyl ester as a pale yellow foam.

(f)

(4S)-1-[[[3-(Benzoylamino)-2-hydroxy-4-phenylbutyl]methylamino]acetyl]-4-(phenylthio)-L-proline, diphenylmethyl ester To a chilled solution of the ester product from part (e) (0.58 g., 0.8 mmole) is added cerium (III) chloride.8 water (0.31 g., 0.8 mmole) and the reaction mixture is stirred until a clear solution is obtained (approximately 5 minutes). Sodium borohydride (0.031 g., 0.8 mmole) is added portionwise over a 5 minute period. After the addition is completed, the reaction mixture is stirred at 0° for 10 minutes, poured into aqueous saturated ammonium chloride (50 ml.) and extracted with ethyl acetate (3×50 ml.). The combined ethyl acetate extracts are dried (Na2SO4) and concentrated under reduced pressure. The residue is flash chromatographed (Whatman LPS-1 silica gel, 3% methanol/methylene chloride) to give 0.28 g. of (4S)-1-[[[3-(benzoylamino)-2-hydroxy-4-phenylbutyl]methylamino]acetyl]-4-(phenylthio)-L-proline, diphenylmethyl ester (mixture of 4 isomers) as a pale yellow foam.

(g)

(4S)-1-[[[3-(Benzoylamino)-2-hydroxy-4-phenylbutyl]methylamino]acetyl]-4-(phenylthio)-L-proline, monohydrochloride The ester product from part (f) (0.26 g., 0.35 mmole) is treated with 1.4N hydrochloric acid/acetic acid (10 ml.). After stirring for 1.5 hours at room temperature, the reaction mixture is concentrated under reduced pressure and the oily residue is triturated with ether (4x) yielding 0.19 g. of off-white solids of (4S)-1-[[[3-(benzoylamino)-2-hydroxy-4-phenylbutyl]methylamino]acetyl]-4-(phenylthio)-L-proline, monohydrochloride as a mixture of isomers; m.p. 127°–150° (slow decomposition).

$R_f$ 0.45, 0.54 (silica gel, n-butanol:acetic acid:water; 3:1:1).

Anal. calc'd. for $C_{31}H_{35}N_3O_5S \cdot HCl \cdot 0.52\ H_2O$: C, 61.28; H, 6.14; N, 6.92; S, 5.28; Cl, 5.83. Found: C, 61.28; H, 5.94; N, 6.91; S, 5.25; Cl, 5.64.

EXAMPLE 3

(S)-1-[[[3-(Benzoylamino)-2-hydroxy-4-phenylbutyl]methylamino]acetyl]-L-proline, monohydrochloride, isomer A (a) [N-[(Phenylmethoxy)carbonyl]methylamino]acetic acid To a chilled (0°) solution of sarcosine (44.5 g., 0.5 mole) in 2N sodium hydroxide (250 ml.) is added with stirring simultaneously benzyl chloroformate (102.5 g., 0.55 mole) and 4N sodium hydroxide (125 ml.) over a one hour period. After stirring overnight (0° to room temperature), the reaction mixture is washed with ether (twice), the aqueous layer is acidified to pH2 with 10% potassium bisulfate, and extracted with ethyl acetate (3×). The combined ethyl acetate extracts are dried (Na2SO4) and concentrated under reduced pressure into an oily residue. The residue is redissolved in ether and the product is precipitated with petroleum ether to give 89.5 g. of [N-[(phenylmethoxy)carbonyl]methylamino]acetic acid.

(b)

1-[[N-[(Phenylmethoxy)carbonyl]methylamino]acetyl]-L-proline, 1,1-dimethylethyl ester To a solution of [N-[(phenylmethoxy)carbonyl]methylamino]acetic acid (22.3 g., 100 mmole) in distilled tetrahydrofuran (200 ml.) is added L-proline, 1,1-dimethylethyl ester (17.1 g., 100 mmole), dicyclohexylcarbodiimide (20.6 g., 100 mmole), and 1-hydroxybenzotriazole hydrate (15.3 g., 100 mmole). The reaction mixture is stirred overnight, the precipitated dicyclohexylurea is filtered off, and the filtrate is concentrated. The residue is dissolved in ethyl acetate (300 ml.), and washed with saturated sodium bicarbonate (2×150 ml.), 10% potassium bisulfate (2×150 ml.), water (2×), dried (Na2SO4), and concentrated to give 25.5 g. of 1-[[N-[(phenylmethoxy)carbonyl]methylamino]acetyl]-L-proline, 1,1-dimethylethyl ester as an oily residue.

(c) 1-[[Methylamino]acetyl]-L-proline, 1,1-dimethylethyl ester

A solution of the ester product from part (b) (5.0 g., 13.3 mmole) in 95% ethanol (50 ml.) containing 10% palladium on carbon catalyst (0.5 g.) is hydrogenated overnight under atmospheric pressure. The catalyst is filtered, washed with 95% ethanol, and the washings and filtrate are concentrated to give 2.75 g. of 1-[[methylamino]acetyl]-L-proline, 1,1-dimethylethyl ester as an oily residue.

(d)
(S)-1-[[[3-(Benzoylamino)-2-oxo-4-phenylbutyl]methylamino]acetyl]-L-proline, 1,1-dimethylethyl ester A mixture of the ester product from part (c) (2.75 g., 11.35 mmole), (S)-N-[3-chloro-2-oxo-1-(phenylmethyl)propyl]benzamide (3.54 g., 11.35 mmole), excess sodium bicarbonate, sodium iodide (1.69 g., 11.35 mmole) in dimethylformamide (40 ml.) is stirred at room temperature under nitrogen atmosphere overnight. The reaction mixture is poured into water (100 ml.) and extracted with ethyl acetate (3×50 ml.). The combined ethyl acetate extracts are washed with saturated sodium bicarbonate (2×), water (3×), dried ($Na_2SO_4$), and concentrated under reduced pressure into an oily residue (2.7 g., yellow oil). Flash chromatography (Merck silica gel; 2% methanol/chloroform) gives 3.95 g. of (S)-1-[[[3-(benzoylamino)-2-oxo-4-phenylbutyl]methylamino]acetyl]-L-proline, 1,1-dimethylethyl ester as a pale yellow foam; $[\alpha]_D^{25}$ −42.8° (c=0.53, chloroform).

(e)
(3S-1-[[[3-(Benzoylamino)-2-hydroxy-4-phenylbutyl]methylamino]acetyl]-L-proline, 1,1-dimethylethyl ester To a chilled (0°) solution of the ester product from part (d) (1.77 g., 3.5 mmole) in methanol (20 ml.) is added cerium (III) chloride.8 water (1.37 g., 3.5 mmole) and the reaction mixture is stirred until a clear solution is obtained (approximately 5 minutes). Sodium borohydride (0.26 g., 7 mmole) is added portionwise over a 5 minute period. After the addition is complete, the reaction mixture is stirred at 0° for 15 minutes, poured into aqueous saturated ammonium chloride (50 ml.) and extracted with ethyl acetate (3×50 ml.). The combined ethyl acetate extracts are dried ($Na_2SO_4$) and concentrated under reduced pressure to give 1.4 g. of (3S)-1-[[[3-(benzoylamino)-2-hydroxy-4-phenylbutyl]methylamino]acetyl]-L-proline, 1,1-dimethylethyl ester as an oily residue.

(f)
(3S)-1-[[[3-(Benzoylamino)-2-hydroxy-4-phenylbutyl]methylamino]acetyl]-L-proline, 1,1-dimethylethyl ester, isomer A The diastereomeric mixture of the ester product of part (e) is flash chromatographed (Whatman LPS-1 silica gel; 1% methanol/dichloromethane). The fractions containing the higher $R_f$ diastereomer are combined and after removal of the solvent at reduced pressure give 0.59 g. of (3S)-1-[[[3-(benzoylamino)-2-hydroxy-4-phenylbutyl]methylamino]acetyl]-L-proline, 1,1-dimethylethyl ester, isomer A as a colorless foam; $R_f$ 0.28; $[\alpha]_D^{25}$ −99.8° (c=0.5, methanol).

(g)
(3S)-1-[[[3-(Benzoylamino)-2-hydroxy-4-phenylbutyl]methylamino]acetyl]-L-proline, monohydrochloride, isomer A The ester product from part (f) (0.57 g., 1.12 mmole) is treated with 1.4 N hydrochloric acid/acetic acid (15 ml.). After stirring for 1.5 hours at room temperature, the reaction mixture is concentrated under reduced pressure and the oily residue triturated with ether (4x) yielding 0.53 g. of (3S)-1-[[[3-(benzoylamino)-2-hydroxy-4-phenylbutyl]methylamino]acetyl]-L-proline, monohydrochloride, isomer A, as off-white solids, m.p. 120°-155° (slow decomposition); $[\alpha]_D^{25}$ −100.9° (c=0.525, methanol). $R_f$ 0.25 (silica gel; n-butanol:acetic acid:water; 3:1:1).

Anal. calc'd. for $C_{25}H_{31}N_3O_5 \cdot HCl \cdot 0.3 H_2O$: C, 60.58; H, 6.63; N, 8.48; cl, 7.15. Found: C, 60.58; H, 6.69; N, 8.36; Cl, 6.89.

EXAMPLE 4

(3S)-1-[[[3-(Benzoylamino)-2-hydroxy-4-phenylbutyl]methylamino]acetyl]-L-proline, monohydrochloride, isomer B (a) (3S)-1-[[[3-(Benzoylamino)-2-hydroxy-4-phenylbutyl]methylamino]acetyl]-L-proline, 1,1-dimethylethyl ester, isomer B The diastereomeric mixture of the ester product from Example 3(e) is flash chromatographed (Whatman LPS-1 silica gel; 1% methanol/dichloromethane). The fractions containing the lower $R_f$ diastereomer are combined and after removal of the solvent at reduced pressure give 0.33 g. of (3S)-1-[[[3-(benzoylamino)-2-hydroxy-4-phenylbutyl]methylamino]acetyl]-L-proline, 1,1-dimethylethyl ester, isomer B as a colorless foam; $[\alpha]_D^{25}$ −63.0° (c=0.5, methanol). $R_f$ 0.20 (7% methanol/dichloromethane).

(b)
(3S)-1-[[[3-(Benzoylamino)-2-hydroxy-4-phenylbutyl]methylamino]acetyl]-L-proline, monohydrochloride, isomer B The product from part (a) (0.32 g., 0.63 mmole) is treated with 1.4N hydrochloric acid/acetic acid (10 ml.). After stirring for 2 hours at room temperature, the reaction mixture is concentrated at reduced pressure and the oily residue is triturated with ether (3×) to yield 0.22 g. of (3S)-1-[[[3-(benzoylamino)-2-hydroxy-4-phenylbutyl]methylamino]acetyl]-L-proline, monohydrochloride, isomer B as white solids, m.p. 120°-175° (slow decomposition); $[\alpha]_D^{25}$ −54.2° (c=0.64, methanol). $R_f$ 0.25 (silica gel; n-butanol:acetic acid:water; 3:1:1).

Anal. calc'd. for $C_{25}H_{31}N_3O_5 \cdot HCl \cdot 0.96 H_2O$: C, 59.20; H, 6.74; N, 8.29; Cl, 6.99. Found: C, 59.20; H, 6.51; N, 8.12; Cl, 6.72.

EXAMPLE 5

(3S)-N-[N-[3-(Benzoylamino)-2-hydroxybutyl]-L-phenylalanyl]-L-leucine, monohydrochloride, isomer A (a) (S)-(3-Diazo-1-methyl-2-oxopropyl)carbamic acid, 1,1-dimethylethyl ester To a vigorously stirred solution of N-[(1,1-dimethylethoxy)carbonyl]-L-alanine (15.14 g., 80 mmole) and N-methylmorpholine (8.80 ml., 80 mmole) in dry tetrahydrofuran (80 ml.) at −15° under argon is added a solution of isobutyl chloroformate (10.37 ml., 80 mmole) in tetrahydrofuran (10 ml.) while maintaining the reaction temperature below −12°. After the addition is complete, the reaction mixture is stirred for 14 minutes, diluted with anhydrous ether (250 ml., prechilled to −20°), and quickly filtered. Approximately one-fourth of the filtrate is transferred to a separatory funnel (the remainder is kept chilled) and added rapidly to a gently stirred, chilled (0°) solution of diazomethane (160 mmole). Additional chilled portions are transferred to the separatory funnel until the entire solution has been added (approximately 10 minutes). The resulting solution is stirred for 2 hours, warming gently to room temperature, then purged with nitrogen for 1 hour, washed with chilled half-saturated sodium bicarbonate (2×100 ml.) and water (3×50 ml.), dried (Na2SO4), and evaporated to a yellow semi-crystalline residue. Two recrystallizations from ethyl acetate-petroleum ether yield 10.29 g. of product as yellow plates; m.p. 99°–102° plus an additional crop of 1.33 g.; m.p. 97.5°–101°. A portion is recrystallized once more giving an analytically pure sample of (S)-(3-diazo-1-methyl-2-oxopropyl)carbamic acid, 1,1-dimethylethyl ester; m.p. 102°–103°.

(b) (S)-(3-Chloro-1-methyl-2-oxopropyl)carbamic acid, 1,1-dimethylethyl ester

Hydrogen chloride gas is slowly bubbled into a chilled (0°–5°) solution of (S)-(3-diazo-1-methyl-2-oxopropyl)carbamic acid, 1,1-dimethylethyl ester (9.58 g., 44.9 mmole) in 400 ml. of ether until the solution is colorless and nitrogen evolution ceases. The solution is refrigerated for one hour, then washed with ice-water (3×50 ml.), dried (Na2SO4), and evaporated to yield 9.87 g. of (S)-(3-chloro-1-methyl-2-oxopropyl)carbamic acid, 1,1-dimethylethyl ester as a white crystalline solid; m.p. 64°–66.5°. A portion is recrystallized from ether-petroleum ether to give an analytical sample; m.p. 65.5°–67°.

(c) (S)-3-Amino-1-chloro-2-butanone, monohydrochloride

A solution of (S)-(3-chloro-1-methyl-2-oxopropyl)-carbamic acid, 1,1-dimethylethyl ester (9.25 g., 41.7 mmole) in 85 ml. of 1.5N hydrochloric acid/acetic acid is allowed to stand for 20 minutes at 10°–15°. The resulting crystalline mass is diluted with ether (250 ml.), filtered, washed with ether (50 ml.) and dried to yield 6.45 g. of (S)-3-amino-1-chloro-2-butanone, monohydrochloride as a white crystalline solid; m.p. 129°–131° (decomposition begins at approximately 127°).

(d) (S)-3-(Benzoylamino)-1-chloro-2-butanone

To a vigorously stirred suspension of (S)-3-amino-1-chloro-2-butanone, monohydrochloride (3.0 g., 19.0 mmole) in 150 ml. of tetrahydrofuran at 0°–5° is added, sequentially, benzoyl chloride (2.2 ml., 19.0 mmole), triethylamine (2.65 ml., 19.0 mmole), and sodium bicarbonate (1.6 g., 19.0 mmole). The reaction mixture is stirred for 15 minutes in the cold and then for 2 hours at room temperature. The solvent is evaporated and the residue is partitioned between ethyl acetate (400 ml.) and ice-water (40 ml.). The organic layer is washed with 5% potassium bisulfate (2×30 ml.) and water (3×30 ml.), then dried and evaporated. The resulting crystalline residue is recrystallized from benzene-petroleum ether giving three crops of comparable purity totaling 3.67 g.; m.p. 119.5°–121.5° (first crop), 118°–119.5° (third crop). A portion is recrystallized once more giving an analytically pure sample of (S)-3-(benzoylamino)-1-chloro-2-butanone; m.p. 119.5°–121°.

(e) (S)-N-[N-[3-(benzoylamino)-2-oxobutyl]-L-phenylalanyl]-L-leucine, 1,1-dimethylethyl ester To a stirred solution of L-phenylalanyl-L-leucine, 1,1-dimethylethyl ester (3.48 g., 10 mmole) in 20 ml. of dimethylformamide (under argon) is added (S)-3-(benzoylamino)-1-chloro-2-butanone (2.26 g., 10 mmole), sodium iodide (375 mg., 2.5 mmole), and sodium bicarbonate (840 mg., 10 mmole). The reaction mixture is stirred for 10 minutes and then an additional 20 ml. of dimethylformamide is added. After 2.5 hours the reaction has completed. The dimethylformamide is evaporated in vacuo and the residue is taken up into ether (35 ml.), washed with half-saturated sodium bicarbonate (2×50 ml.) and brine (2×25 ml.), dried (mixture of MgSO4 and Na2SO4), and evaporated to give 6.02 g. of a yellow oil which darkens to orange over 2 hours. This material is applied to a column of 300 g. of silica gel (230–400 mesh) and eluted with ethyl acetate-hexane (3:2). Fractions 21–27 (approximately 50 ml. each) are pooled giving 2.26 g. of crude product. This material is applied to a second column of silica gel (LPS-1, 130 g.) and eluted with 3 l. of hexane-ethyl acetate (2:1) then 2 l. of hexane-ethyl acetate (1:1). Fractions 61–100 (approximately 30 ml. each) are pooled and evaporated yielding 1.39 g. of product. One recrystallization from ethyl acetate gives 900 mg. of (S)-N-[N-[3-(benzoylamino)-2-oxobutyl]-L-phenylalanyl]-L-leucine, 1,1-dimethylethyl ester as a white, powdery solid; m.p. 46°–50°.

(f) (3S)-N-[N-[3-(Benzoylamino)-2-hydroxybutyl]-L-phenylalanyl]-L-leucine, 1,1-dimethylethyl ester To a solution of (S)-N-[N-[3-(benzoylamino)-2-oxobutyl]-L-phenylalanyl]-L-leucine,1,1-dimethylethyl ester (1.05 g., 2 mmole) in 10 ml. of methanol at 0° is added sodium borohydride (76 mg., 2 mmole) in two portions. After 10 minutes, acetone (approximately 5 drops) is added and then the solvent is evaporated. The colorless residue is taken up into ethyl acetate (75 ml.), washed with water until the extracts are neutral, washed with brine, dried (Na2SO4), and evaporated to give 1.08 g. of (3S)-N-[N-[3-(benzoylamino)-2-hydroxybutyl]-L-phenylalanyl]-L-leucine, 1,1-dimethylethyl ester as a white foam.

(g) (3S)-N-[N-[3-(Benzoylamino)-2-hydroxybutyl]-L-phenylalanyl]-L-leucine, 1,1-dimethylethyl ester, isomer A The diastereomeric mixture of the ester product from part (f) (1.08 g.) is applied to a column of silica gel (Merck, 230–400 mesh, 120 g.) and eluted with ethyl acetate-hexane (4:1). Fractions 29–44 (approximately 10 ml. each) are pooled and concentrated to give 0.61 g. of (3S)-N-[N-[3-(benzoylamino)-2-hydroxybutyl]-L-phenylalanyl]-L-leucine, 1,1-dimethylethyl ester, isomer A.

(h) (3S)-N-[N-[3-(Benzoylamino)-2-hydroxybutyl]-L-phenylalanyl]-L-leucine, monohydrochloride, isomer A A solution of resolved ester product of part (g) (0.57 g., 1.08 mmole) in 15 ml. of approximately 2N hydrochloric acid in acetic acid is allowed to stand at room temperature for 1.5 hours. The solvent is evaporated in vacuo and the colorless residue is triturated with ethyl ether to give 504 mg. of a white solid. This material is applied to a column of HP-20 in 60% methanol in 0.01N hydrochloric acid and eluted with the same solvent. Fractions 13–23 (approximately 5 ml. each) are pooled, filtered, and evaporated. The residue is chased twice with methanol producing a white solid which is triturated with ethyl ether and collected to give 324 mg. of (3S)-N-[N-[3-(benzoylamino)-2-hydroxybutyl]-L-phenylalanyl]-L-leucine, monohydrochloride, isomer A as a white solid, m.p. 168°–171.5° (with loss of solvent approximately 135°–140°); $[\alpha]_D^{25}$ +10.4° (c=1.02, dimethylformamide). $R_f$ 0.31 (silica gel; chloroform:methanol:acetic acid; 10:1:1).

Anal. calc'd. for $C_{26}H_{35}N_3O_5.HCl.0.39H_2O$: C, 60.87; H, 7.22; N, 8.19; Cl, 6.91. Found: C, 60.86; H, 7.29; N, 8.02; Cl, 6.74.

EXAMPLE 6

(3S)-N-[N-[3-(Benzoylamino)-2-hydroxybutyl]-L-phenylalanyl]-L-leucine, monohydrochloride, isomer B (a)

(3S)-N-[N-[3-(Benzoylamino)-2-hydroxybutyl]-L-phenylalanyl]-L-leucine, 1,1-dimethylethyl ester, isomer B The diastereomeric mixture of the ester product from Example 5(f) (1.08 g.) is applied to a column of silica gel (Merck 230–400 mesh, 120 g.) and eluted with ethyl acetate-hexane (4:1). Fractions 61–97 (approximately 10 ml. each) are pooled and concentrated to give 230 mg. of isomer B contaminated with a small amount of isomer A. This material is streaked onto 2 preparative TLC plates (Merck silica 60 F-254, 20×20 cm., 2 mm. thickness) and eluted once with ethyl acetate. The lower 80% of the major band is scraped and eluted with ethyl acetate yielding, after removal of the solvent, 189 mg. of (3S)-N-[N-[3-(benzoylamino)-2-hydroxybutyl]-L-phenylalanyl]-L-leucine, 1,1-dimethylethyl ester, isomer B; $R_f$ 0.30 (silica gel; ethyl acetate).

(b)

(3S)-N-[N-[3-(Benzoylamino)-2-hydroxybutyl]-L-phenylalanyl]-L-leucine, monohydrochloride, isomer B A solution of the resolved ester product from part (a) (189 mg., 0.36 mmole) in 10 ml. of approximately 2N hydrochloric acid in acetic acid is allowed to stir at room temperature during which time a white precipitate separates. The solvent is evaporated in vacuo and the white residue is triturated with ethyl ether and filtered yielding 159 mg. of (3S)-N-[N-[3-(benzoylamino)-2-hydroxybutyl]-L-phenylalanyl]-L-leucine, monohydrochloride, isomer B as a white solid; m.p. 227°–229° (with slow decomposition at greater than 185°); $[\alpha]_D^{25}$ −13° (c=1.0, dimethylformamide). $R_f$ 0.25 (silica gel; chloroform:methanol:acetic acid; 10:1:1).

Anal. calc'd. for $C_{26}H_{35}N_3O_5.HCl.0.5H_2O$: C, 60.63; H, 7.24; N, 8.16; Cl, 6.88. Found: C, 60.64; H, 7.13; N, 8.10; Cl, 6.81.

EXAMPLE 7

(3S)-1-[N-[3-(Benzoylamino)-2-hydroxy-4-phenylbutyl]-L-lysyl]-L-proline, dihydrochloride (a)

1-[$N^2$-[(1,1-Dimethylethoxy)carbonyl]-$N^6$-[(phenylmethoxy)carbonyl]-L-lysyl]-L-proline, phenylmethyl ester To a solution of $N^2$-[(1,1-dimethylethoxy)carbonyl]-$N^6$-[(phenylmethoxy)carbonyl]-L-lysine (19.0 g., 50 mmole) in tetrahydrofuran (250 ml., distilled) is added L-proline, phenylmethyl ester, hydrochloride (12.1 g., 50 mmole), dicyclohexylcarbodiimide (10.3 g., 50 mmole), 1-hydroxybenzotriazole hydrate (7.56 g., 50 mmole), and diisopropylethylamine (8.71 ml., 50 mmole). The reaction mixture is stirred overnight, the precipitated dicyclohexyl urea is filtered, and the filtrate is concentrated. The residue is dissolved in ethyl acetate (300 ml.) and washed with saturated sodium bicarbonate (2×150 ml.), 10% potassium bisulfate (2×150 ml.), and water (twice), dried ($Na_2SO_4$), and concentrated to give 23.2 g. of 1-[$N^2$-[(1,1-dimethylethoxy)carbonyl]-$N^6$-[(phenylmethoxy)carbonyl]-L-lysyl]-L-proline, phenylmethyl ester as an oily residue.

(b)

1-[$N^6$-[(Phenylmethoxy)carbonyl]-L-lysyl]-L-proline, phenylmethyl ester, hydrochloride To a cold (0°) solution of the ester product from part (a) (23.2 g., 40.8 mmole) in dichloromethane (50 ml.) is added trifluoroacetic acid (25 ml.) containing anisole (0.25 ml.). After stirring for 4.5 hours, the volatiles are removed in vacuo and the residue is chased with toluene (three times). The oily residue is dissolved in ether (100 ml.) and treated with hydrochloric acid/ether solution. The resulting oily product is triturated with hexane to give 17.0 g. of 1-[$N^6$-[(phenylmethoxy)carbonyl]-L-lysyl]-L-proline, phenylmethyl ester, hydrochloride as a pale yellow foam.

(c)

(S)-1-[$N^2$-[3-(Benzoylamino)-2-oxo-4-phenylbutyl]-$N^6$-[(phenylmethoxy)carbonyl]-L-lysyl]-L-proline, phenylmethyl ester To a solution of 1-[$N^6$-[(phenylmethoxy)carbonyl]-L-lysyl]-L-proline, phenylmethyl ester, hydrochloride (5.03 g., 10 mmole) in dimethylformamide (15 ml.) is added diisopropylethylamine (1.74 ml., 10 mmole). The reaction mixture is stirred for 5 minutes and (S)-N-[3-chloro-2-oxo-1-phenylmethyl)propyl]benzamide (3.0 g., 10.0 mmole), excess sodium bicarbonate, and sodium iodide (1.5 g., 10.0 mmole) are added. The resulting mixture is stirred at room temperature under a nitrogen atmosphere overnight. The reaction mixture is then poured into water (100 ml.) and extracted with ethyl acetate (3×50 ml.). The combined ethyl acetate extracts are washed with saturated sodium bicarbonate (twice) and water (three times), dried ($Na_2SO_4$), and concentrated under reduced pressure into an oily residue (5.0 g., yellow oil). Flash chromatography (LPS-1 silica gel; 1% methanol/chloroform) gives 0.9 g. of (S)-1-[$N^2$-[3-(benzoylmaino)-2-oxo-4-phenylbutyl]-$N^6$-[(phenylmethoxy)carbonyl]-L-lysyl]-L-proline, phenylmethyl ester as a pale yellow foam. $R_f$ 0.35 (silica gel; 6% methanol/chloroform).

(d)

(S)-1-[$N^2$-[3-(Benzoylamino)-2-oxo-4-phenylbutyl]-$N^2$-[(phenylmethoxy)carbonyl]-$N^6$-[(phenylmethoxy)carbonyl]-L-lysyl]-L-proline, phenylmethyl ester To a chilled (0°) solution of the ester product from part (c) (0.8 g., 1.15 mmole) in dichloromethane (25 ml.) is added diisopropylethylamine (0.19 ml., 1.15 mmole) and benzyl chloroformate (0.16 ml., 1.15 mmole). After stirring overnight (0° to room temperature), the reaction mixture is diluted with ethyl acetate (100 ml.), washed with saturated sodium bicarbonate (twice), 10% potassium bisulfate (twice) and water (twice), and concentrated under reduced pressure. The oily residue (0.9 g.) is purified by flash chromatography (LPS-1 silica gel, 3% methanol/chloroform) to give 0.6 g. of (S)-1-[$N^2$-[3-(benzoylamino)-2-oxo-4-phenylbutyl]-$N^2$-[(phenylmethoxy)carbonyl]-$N^6$-[(phenylmethoxy)carbonyl]-L-lysyl]-L-proline, phenylmethyl ester as a pale yellow foam. $R_f$ 0.69 (silica gel, 6% methanol/chloroform).

(e) (3S)-1-[$N^2$-[3-(Benzoylamino-2-hydroxy-4-phenylbutyl]-$N^2$-[(phenylmethoxy)carbonyl]-$N^6$-[(phenylmethoxy)carbonyl]-L-lysyl]-L-proline, phenylmethyl ester To a cold (0°) solution of the ester product from part (d) (0.64 g., 0.75 mmole) in tetrahydrofuran/water (9:1, 10 ml.) is added cerium (III) chloride.8 water (0.29 g., 0.25 mmole) and the reaction mixture is stirred until a clear solution is obtained (approximately 5 minutes). Sodium borohydride (0.028 g., 0.75 mmole) is added portionwise over a five minute period. After the additions is completed, the reaction mixture is stirred at 0° for 25 minutes, poured into aqueous saturated ammonium chloride (50 ml.) and extracted with ethyl acetate (3×50 ml.). The combined ethyl acetate extracts are dried ($Na_2SO_4$) and concentrated under reduced pressure to give 0.55 g. of the diastereomeric mixture (3S)-1-[$N^2$-[3-(benzoylamino)-2-hydroxy-4-phenylbutyl]-$N^2$-[(phenylmethoxy)carbonyl]-$N^6$-[(phenylmethoxy)carbonyl]-L-lysyl]-L-proline, phenylmethyl ester as an oily residue.

(f) (3S)-1-[N-[3-(Benzoylamino)-2-hydroxy-4-phenylbutyl]-L-lysyl]-L-proline, dihydrochloride A solution of the ester product from part (e) (0.55 g., 0.64 mmole) in 95% ethanol (50 ml.) containing 10% palladium on carbon catalyst (0.2 g.) is hydrogenated under atmospheric pressure overnight. The catalyst is filtered, washed with 95% ethanol, and the filtrate and the washings are concentrated into an oily residue. This is treated for 5 minutes with 1.4N hydrochloric acid/acetic acid (10 ml.). The reaction mixture is concentrated under reduced pressure and the residue triturated with ether to yield 0.31 g. of an off-white solid residue. This crude product is purified on an HP-20 column (5% methanol/0.01N hydrochloric acid→90% methanol/0.01N hydrochloric acid) to give 0.08 g. of (3S)-1-[N-[3-(benzoylamino)-2-hydroxy-4-phenylbutyl]-L-lysyl]-L-proline, hydrochloride as a white solid; m.p. 67°–80°. $R_f$ 0.15 (silica gel; n-butanol:acetic acid:water: 3:1:1).

Anal. calc'd. for $C_{28}H_{38}N_4O_5 \cdot 2HCl \cdot 1.12H_2O$: C, 55.71; H, 6.95; N, 9.31; Cl, 11.75. Found: C, 55.71; H, 7.05; N, 9.28; Cl, 11.87.

EXAMPLES 8–42

Following the procedure of Examples 1 to 7, the diketo ester compound shown in Col. I is treated with a reducing agent, preferably sodium borohydride, to give the hydroxy substituted ester product shown in Col. II. Removal of the ester group yields the final product wherein $R_6$ is hydrogen.

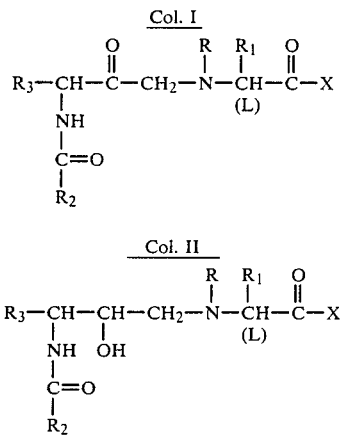

| Example | R₃ | R₂ | R₁ | X | R |
|---|---|---|---|---|---|
| 8 | CH₂-phenyl | phenyl | H— | dithiolane-CH₂-CH(COOC(CH₃)₃)(L)-N(H)— | cyclohexyl |
| 9 | CH₂-phenyl | 4-F-phenyl-CH₂— | H— | cyclohexyl-CH₂-CH(COOC(CH₃)₃)(L)-N(H)— | phenyl-CH₂— |
| 10 | (CH₂)₄-phenyl | 4-CH₃-phenyl | H— | phenyl-CH(CH₂-)-CH(COOC(CH₃)₃)(L)-N(H)— (H₂C) | H₃C— |
| 11 | CH₂-thienyl | phenyl-(CH₂)₂— | H₃C— | tetrahydroisoquinoline-CH(COOC(CH₃)₃)(L)-N— | H₃C— |
| 12 | CH₂-pyridyl | phenyl | H₃C— | phenyl-(CH₂)₃-CH(COOCH₂(L))-N(H)— | H— |

-continued

| Example | R₃ | R₂ | R₁ | X | R |
|---|---|---|---|---|---|
| 13 | H₃CO-C₆H₄-CH₂- | C₆H₅- | H₃C- | -N(cyclic butyl)-CH-COOC(CH₃)₃ (L), H | H- |
| 14 | C₆H₅-CH₂- | C₆H₅- | H- | -N-CH₂-CH(4-F-C₆H₄-O-)-CH-COOC(CH₃)₃ (L), H | H₃C- |
| 15 | C₆H₅-CH₂- | C₆H₅- | H₃C- | -N-CH₂-CH(4-F-C₆H₄-O-)-CH-COOC(CH₃)₃ (L), H | H- |
| 16 | C₆H₅-CH₂- | C₆H₅- | H₃C- | -N-CH₂-CH(C₆H₅)-CH-COOC(CH₃)₃ (L), H | H- |
| 17 | C₆H₅-CH₂- | C₆H₅- | H₃C- | -N-CH₂-CH(cyclohexyl)-CH-COOC(CH₃)₃ (L), H | H- |

-continued

| Example | R₃ | R₂ | R₁ | X | R |
|---|---|---|---|---|---|
| 18 | H₃C— | PhCH₂— | PhCH₂— | PhCH₂—S—CH(CH₂)—N—CH(COOC(CH₃)₃)H (L) | H— |
| 19 | thiophene-CH₂— | 4-Cl-C₆H₄— | H— | H₃C—C(CH₃)(O—CH₂—)(O—)—N—CH(COOC(CH₃)₃)H (L) | H— |
| 20 | H₃C—CH₂— | Ph(CH₂)₂— | H₂C—OH₂C— (PhCH₂OCH₂—) | 2-Ph-C₆H₄—CH₂—N—CH(COOC(CH₃)₃)H (L) | H— |
| 21 | PhCH₂— | pyridyl | O₂N—N=C(NH)—HN—(H₂C)₃— | Ph—CH(OCH₃)—CH₂—N—CH(COOCH₂Ph)H (L) | H— |
| 22 | PhCH₂— | Ph— | PhH₂COCHN(H₂C)₄— (O=) | S—CH₂—N—CH(COOC(CH₃)₃)H (L) | H— |
| 23 | PhCH₂— | Ph— | PhH₂COCHN(H₂C)₂S—(H₂C)₂— (O=) | Ph—(CH₂)₃—N—CH(COOCH₂Ph)H (L) | H— |

-continued

| Example | R₃ | R₂ | R₁ | X | R |
|---------|----|----|----|---|----|
| 24 | PhCH₂– | Ph | 4-(PhCH₂O)-3-(H₂CO)-C₆H₃– (benzyloxy/methoxyphenyl) | PhCOCH₂–CH(NH–)–COOCH₂Ph (H, L) | H– |
| 25 | PhCH₂– | Ph | 3-(PhCH₂O)-4-(H₂CO)-C₆H₃– | CH₂=CH-CH₂-CH(NH–)–COOCH₂Ph (H, L) | H– |
| 26 | Ph(CH₂)₃– | Ph | PhCH₂–N=CH–CH₂– | 1,4-dioxaspiro[4.4] piperidine–COOC(CH₃)₃ (L) | H– |
| 27 | PhCH₂– | 4-CH₃-C₆H₄– | indol-3-ylmethyl (H₂C–indole) | piperidine-2-COOCH₂Ph (H, L) | H– |
| 28 | Ph(CH₂)₂– | PhCH₂– | H₃C–S–(H₂C)₂– | PhS-CH(–(CH₂)₂N–)–COOC(CH₃)₃ (H, L) | H– |

-continued

| Example | $R_3$ | $R_2$ | $R_1$ | X | R |
|---|---|---|---|---|---|
| 29 | Ph-(H₂C)₄-NHCO-CH₂O-C(=O)- (with Ph) | Ph | $H_3C-$ | -N(-(CH₂)₃-)CH(COOC(CH₃)₃)H (L), cyclic | H- |
| 30 | indol-3-ylmethyl (CH₂-indole NH) | Ph | $H_3C-$ | -N(-CH₂-)CH(COOC(CH₃)₃)H (L), with N₃ on ring | H- |
| 31 | PhCH₂- | Ph | $H_3C-$ | -N(Ph)-CH₂-COOC(CH₃)₃ | H- |
| 32 | $H_3C-$ | Ph | H- | -NH-CH(CH₂CH(CH₃)₂)(L)-COOC(CH₃)₃ | $H_3C-$ |
| 33 | $H_5C_2-$ | pyridyl (N in ring) | PhCH₂- | -NH-CH(CH₂-indol-3-yl)-COOC(CH₃)₃ | H- |
| 34 | $H_3C-$ | Ph | $H_3C-$ | -NH-CH(CH₂Ph)(L)-COOC(CH₃)₃ | H- |
| 35 | $H_3C-$ | Ph | PhCH₂- | -NH-CH(CH₂-C₆H₄-OPh)-COOC(CH₃)₃ | H- |

-continued

| Example | R₃ | R₂ | R₁ | X | R |
|---|---|---|---|---|---|
| 36 | H₃C— | C₆H₅ | H₃C— | —NH—CH(L)(CH₂-N=CH-N(CH₂C₆H₅))—COOC(CH₃)₃ | H— |
| 37 | C₆H₅CH₂— | C₆H₅ | H₃C— | lysine-O-CH(CH(CH₃)₂)-O-C(O)-OC₂H₅ (L) | H— |
| 38 | C₆H₅CH₂— | C₆H₅ | H₃C— | cyclohexyl-leucine analog -O-CH(C₆H₁₁)-O-C(O)-OC₂H₅ (L) | H— |
| 39 | C₆H₅CH₂— | C₆H₅ | H— | phenylthio analog -O-CH(CH(CH₃)₂)-O-C(O)-OC₂H₅ (L) | H₃C— |

-continued

| Example | R₃ | R₂ | R₁ | X | R |
|---|---|---|---|---|---|
| 40 | PhCH₂— | Ph— | H₃C— | pyrrolidine-2-CH(COOC₂H₅)(L), N-butylene chain | H— |
| 41 | PhCH₂— | Ph— | H— | 3-(phenylthio)pyrrolidine-2-CH(COOC₂H₅)(L) | H₃C— |
| 42 | PhCH₂— | Ph— | H₃C— | 1,3-dithiolane-spiro-pyrrolidine-2-CH(COOC₃H₇)(L) | H— |

The $R_1$ protecting groups in Examples 20 to 26, the $R_3$ protecting group in Example 29, and the $R_5$ protecting group in Example 35 are removed as the last step in the synthesis. The 4-azidoproline of Example 30 when treated with the reducing agent will yield a 4-aminoproline product. The $R_6$ ester groups shown in Examples 37 to 42 are not removed.

EXAMPLES 43–55

(3S)-1-[N-[3-(Benzoylamino)-2-hydroxy-4-phenylbutyl]-N-[(phenylmethoxy)carbonyl]-L-alanyl]-L-proline, phenylmethyl ester from Example 1 (g) is treated with sodium hydroxide to give (3S)-1-[N-[3-(benzoylamino)-2-hydroxy-4-phenylbutyl]-N-[(phenylmethoxy)carbonyl]-L-alanyl]-L-proline. Treatment with the reagent listed below in Col. I gives the N-protected product shown in Col. II. Removal of the N-protecting group by hydrogenolysis with palladium on carbon catalyst in the presence of hydrochloric acid gives the product shown in Col. III.

Col. II

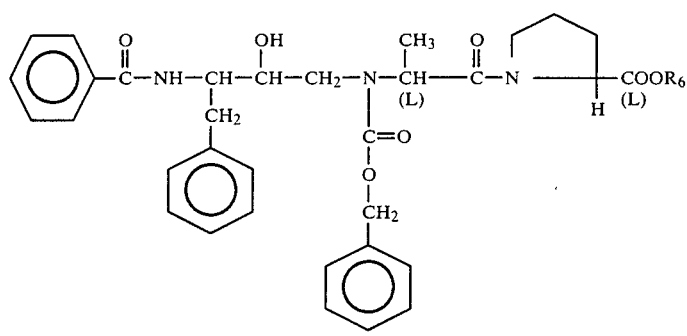

Col. III

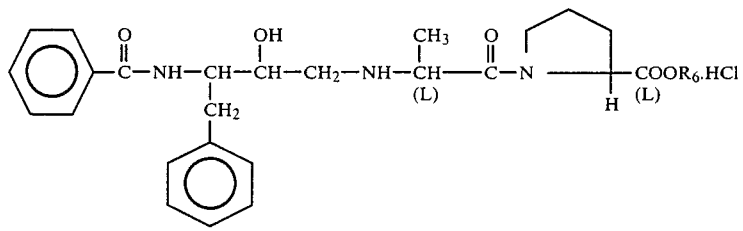

| Example | Col. I | $R_6$ |
|---|---|---|
| 43 | Cl—CH(C₆H₁₁)—O—C(O)—C₂H₅ | —CH(C₆H₁₁)—O—C(O)—C₂H₅ |
| 44 | Cl—CH(CH(CH₃)₂)—O—C(O)—C₂H₅ | —CH(CH(CH₃)₂)—O—C(O)—C₂H₅ |
| 45 | Cl—CH₂—O—C(O)—C(CH₃)₃ | —CH₂—O—C(O)—C(CH₃)₃ |
| 46 | Br—CH₂—O—C(O)—CH₃ | —CH₂—O—C(O)—CH₃ |
| 47 | Cl—CH₂—O—C(O)—C₆H₅ | —CH₂—O—C(O)—C₆H₅ |
| 48 | I—CH₂—C(O)—O—C(CH₃)₃ | —CH₂—C(O)—O—C(CH₃)₃ |
| 49 | I—C(CH₃)₂—C(O)—O—CH₃ | —C(CH₃)₂—C(O)—O—CH₃ |
| 50 | CH(OH)—(CH₂—O—CH₂—C₆H₅)₂ | —CH(CH₂—OH)₂ |
| 51 | CH₂(OH)—CH(O—CH₂—C₆H₅)—CH₂(O—CH₂—C₆H₅) | —CH₂—CH(OH)—CH₂OH |
| 52 | HO—CH₂—CH₂—N(CH₃)₂ | —CH₂—CH₂—N(CH₃)₂ |
| 53 | HO—(CH₂)₂-(2-pyridyl) | —(CH₂)₂-(2-pyridyl) |
| 54 | HO—(CH₂)₃-(2-pyridyl) | —(CH₂)₃-(2-pyridyl) |

| Example | Col. I | $R_6$ |
|---|---|---|
| 55 | HO—(CH$_2$)$_2$—⌬—N | —(CH$_2$)$_2$—⌬—N |

In the case of Examples 50 to 55, the reaction with the reagent listed in Col. I is performed in the presence of a coupling agent such as dicyclohexylcarbodiimide.

EXAMPLE 56

(3S)-1-[N-[3-(Benzoylamino)-2-hydroxy-4-phenyl-butyl]-L-alanyl]-L-proline, sodium salt (3S)-1-[N-[3-(Benzoylamino)-2-hydroxy-4-phenyl-butyl]-L-alanyl]-L-proline, hydrochloride (424 mg., 1 mmole) is dissolved in water (50 ml.). Aqueous sodium bicarbonate (0.1N, 20 ml.) is added and the aqueous solution is lyophilized. It is then dissolved in water (10 ml.) and applied on a column (5 cm. × 60 cm.) of Sephadex chromatography gel G-10 and eluted with water. Fractions containing the desired product are pooled and lyophilized to obtain (3S)-1-[N-[3-(benzoylamino)-2-hydroxy-4-phenylbutyl]-L-alanyl]-L-proline, sodium salt.

EXAMPLE 57

1000 tablets each containing the following ingredients

| | |
|---|---|
| (3S)—1-[N—[3-(Benzoylamino)-2-hydroxy-4-phenylbutyl]-L-alanyl]-L-proline, sodium salt | 100 mg. |
| Corn starch | 50 mg. |
| Gelatin | 7.5 mg. |
| Avicel (microcrystalline cellulose) | 25 mg. |
| Magnesium stearate | 2.5 mg. | are prepared from sufficient bulk quantities by mixing the (3S)-1-[N-[3-(benzoylamino)-2-hydroxy-4-phenyl-butyl]-L-alanyl]-L-proline, sodium salt and corn starch with an aqueous solution of the gelatin. The mixture is dried and ground to a fine powder. The Avicel and then the magnesium stearate are admixed with granulation. This mixture is then compressed in a tablet press to form 1000 tablets each containing 100 mg. of active ingredient.

In a similar manner, tablets containing 100 mg. of the product of any of Examples 1 to 55 can be prepared.

A similar procedure can be employed to form tablets containing 50 mg. of active ingredient.

EXAMPLE 58

Two piece #1 gelatin capsules each containing 50 mg. of (3S)-N-[N-[3-(benzoylamino)-2-hydroxybutyl]-L-phenylalanyl]-L-leucine, sodium salt, isomer A are filled with a mixture of the following ingredients:

| | |
|---|---|
| (3S)—N—[N—[3-(benzoylamino)-2-hydroxybutyl]-L-phenyl-alanyl]-L-leucine, sodium salt, isomer A | 50 mg. |
| Magnesium stearate | 7 mg. |
| Lactose | 193 mg. |
| | 250 mg. |

In a simlar manner capsules containing 50 mg. of the product of any of Examples 1 to 56 can be prepared.

EXAMPLE 59

An injectable solution is prepared as follows:

| | |
|---|---|
| (S)—1-[[[3-(Benzoylamino)-2-hydroxy-4-phenylbutyl]-methylamino]acetyl]-L-proline, sodium salt, isomer B | 500 g. |
| Methyl paraben | 5 g. |
| Propyl paraben | 1 g. |
| Sodium chloride | 25 g. |
| Water for injection | 5 l. |

The active substance, preservatives, and sodium chloride are dissolved in 3 liters of water for injection and then the volume is brought up to 5 liters. The solution is filtered through a sterile filter and aseptically filled into presterilized vials which are closed with presterilized rubber closures. Each vial contains 5 ml. of solution in a concentration of 100 mg. of active ingredient per ml. of solution for injection.

In a similar manner, an injectable solution containing 100 mg. of active ingredient per ml. of solution can be prepared for the product of any Examples 1 to 56.

EXAMPLE 60

1000 tablets each containing the following ingredients:

| | |
|---|---|
| (3S)—1-[N—[3-(Benzoylamino)-2-hydroxy-4-phenylbutyl]-L-lysyl]-L-proline, sodium salt | 100 mg. |
| Avicel | 100 mg. |
| Hydrochlorothiazide | 12.5 mg. |
| Lactose | 113 mg. |
| Cornstarch | 17.5 mg. |
| Stearic acid | 7 mg. |
| | 350 mg. | are prepared from sufficient bulk quantities by slugging the (3S)-1-[N-[3-(benzoylamino)-2-hydroxy-4-phenyl-butyl]-L-lysyl]-L-proline, sodium salt, Avicel, and a portion of the stearic acid. The slugs are ground and passed through a #2 screen, then mixed with the hydrochlorothiazide, lactose, cornstarch, and remainder of the stearic acid. The mixture is compressed into 350 mg. capsule shaped tablets in a tablet press. The tablets are scored for dividing in half.

In a similar manner, tablets can be prepared containing 100 mg. of the product of any of Examples 1 to 56.

What is claimed is:

1. A compound of the formula

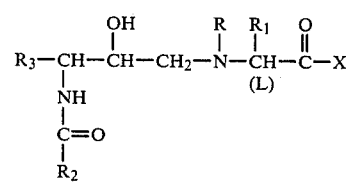

or a pharmaceutically acceptable salt thereof wherein
X is
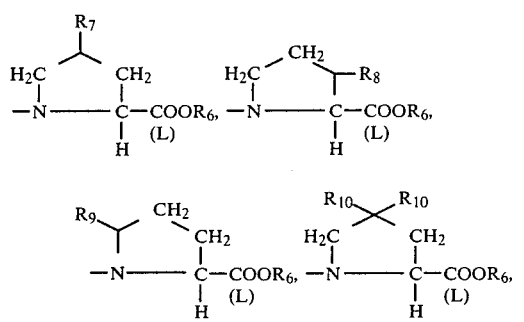
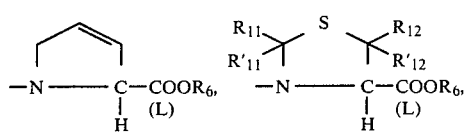
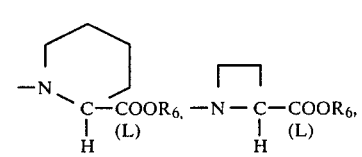
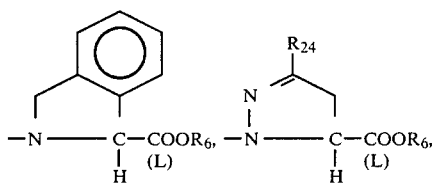
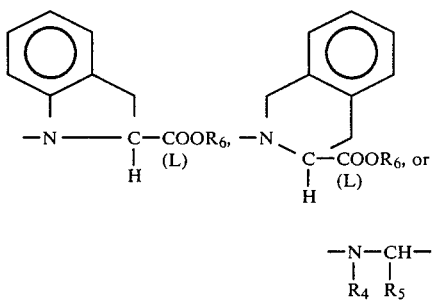
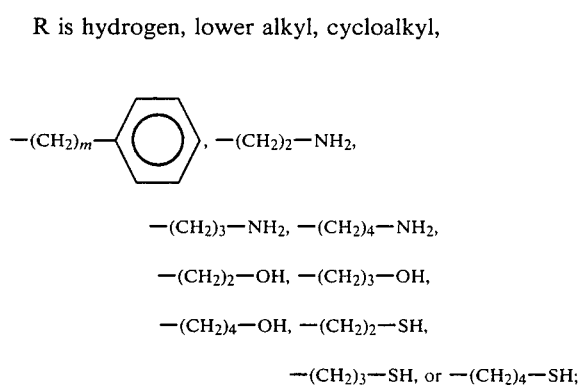
R is hydrogen, lower alkyl, cycloalkyl,
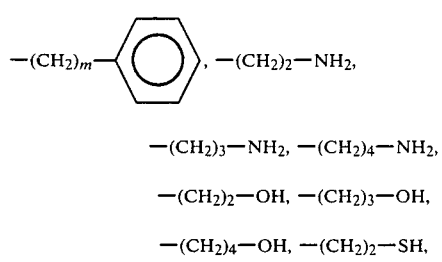, $-(CH_2)_2-NH_2$,
$-(CH_2)_3-NH_2$, $-(CH_2)_4-NH_2$,
$-(CH_2)_2-OH$, $-(CH_2)_3-OH$,
$-(CH_2)_4-OH$, $-(CH_2)_2-SH$,
$-(CH_2)_3-SH$, or $-(CH_2)_4-SH$;
$R_1$ is hydrogen, lower alkyl, halo substituted lower alkyl,
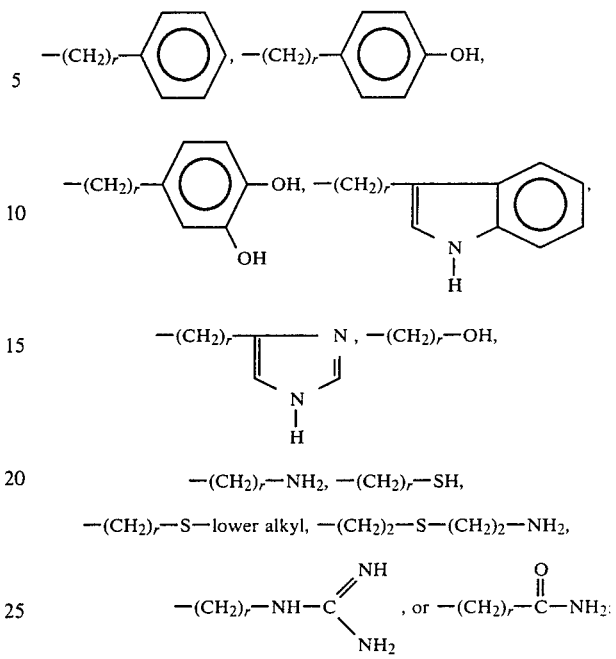
$R_2$ is
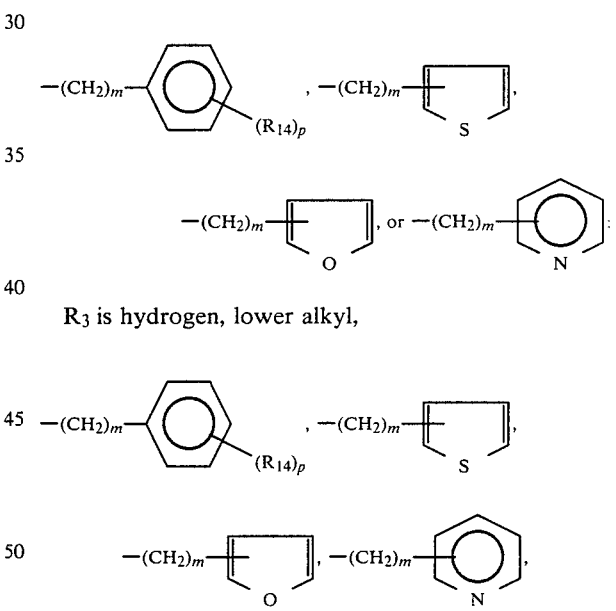
$R_3$ is hydrogen, lower alkyl,
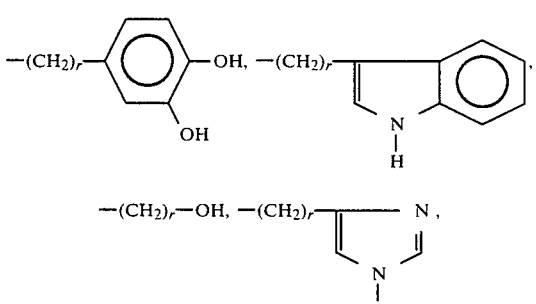
halo substituted lower alkyl, $-(CH_2)_m-$cycloalkyl,
$-(CH_2)_r-$ -continued
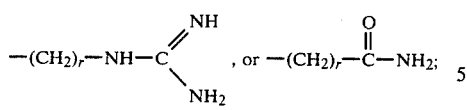
R4 is hydrogen, lower alkyl,
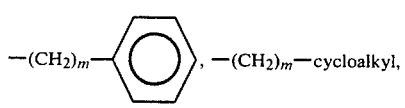
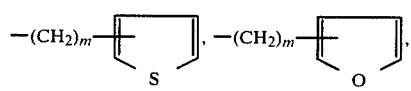
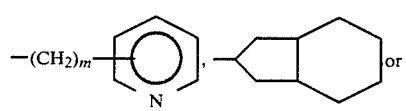
R5 is hydrogen, lower alkyl,
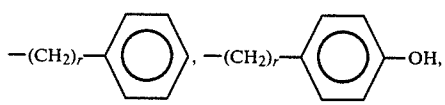
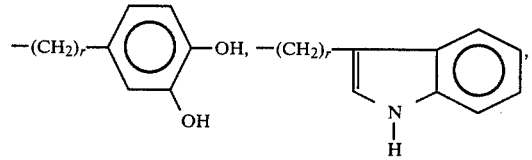
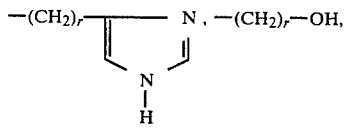
—(CH2)r—NH2, —(CH2)r—SH,
—(CH2)r—S—lower alkyl,
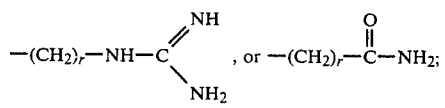
r is an integer from 1 to 4;
R7 is hydrogen, lower alkyl, halogen, hydroxy,
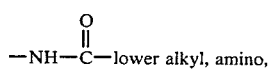
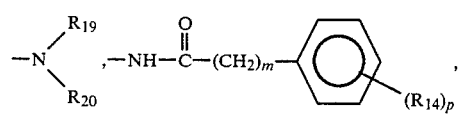
-continued
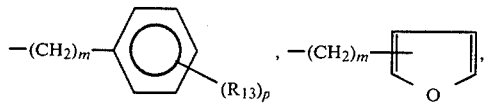
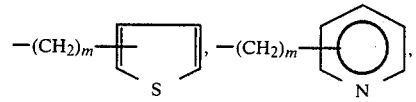
a 1- or 2-naphthyl of the formula
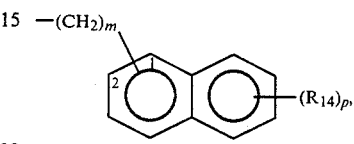
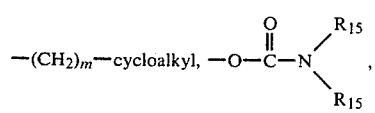
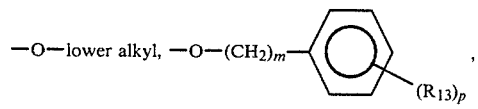
a 1- or 2-naphthyloxy of the formula
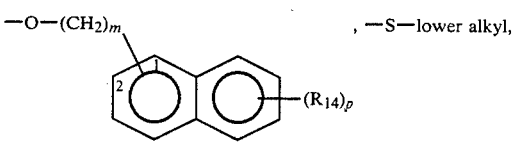
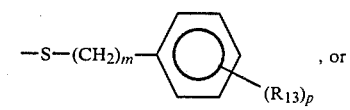
a 1- or 2-naphthylthio of the formula
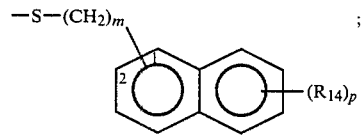
R8 is halogen,
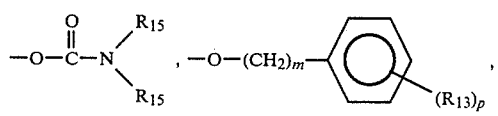
—O-lower alkyl, a 1- or 2-naphthyloxy of the formula
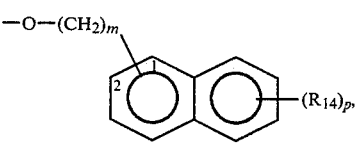

-continued

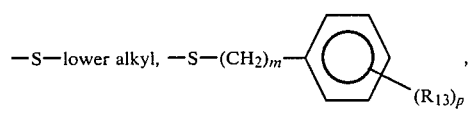

or a 1- or 2-naphthylthio of the formula

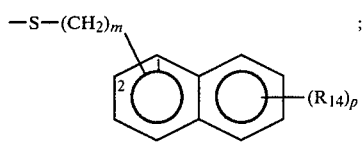

R$_9$ is keto or

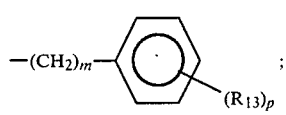

R$_{10}$ is halogen or —Y-R$_{16}$;
R$_{11}$, R$_{11}'$, R$_{12}$ and R$_{12}'$ are independently selected from hydrogen and lower alkyl or R$_{11}'$, R$_{12}$ and R$_{12}'$ are hydrogen and R$_{11}$ is

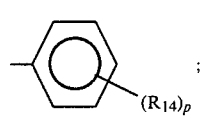

R$_{13}$ is hydrogen, lower alkyl of 1 to 4 carbons, lower alkoxy of 1 to 4 carbons, lower alkylthio of 1 to 4 carbons, chloro, bromo, fluoro, trifluoromethyl, hydroxy, phenyl, phenoxy, phenylthio, or phenylmethyl;
R$_{14}$ is hydrogen, lower alkyl of 1 to 4 carbons, lower alkoxy of 1 to 4 carbons, lower alkylthio of 1 to 4 carbons, chloro, bromo, fluoro, trifluoromethyl, or hydroxy;
m is zero, one, two, three, or four;
p is one, two or three provided that p is more than one only if R$_{13}$ or R$_{14}$ is hydrogen, methyl, methoxy, chloro, or fluoro;
R$_{15}$ is hydrogen or lower alkyl of 1 to 4 carbons;
Y is oxygen or sulfur;
R$_{16}$ is lower alkyl of 1 to 4 carbons,

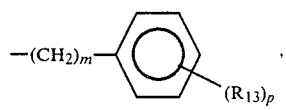

or the R$_{16}$ groups join to complete an unsubstituted 5- or 6-membered ring or said ring in which one or more of the carbons has a lower alkyl of 1 to 4 carbons or a di(lower alkyl of 1 to 4 carbons) substituent;
R$_{19}$ is lower alkyl, benzyl, or phenethyl;
R$_{20}$ is hydrogen, lower alkyl, benzyl or phenethyl;
R$_6$ is hydrogen, lower alkyl, benzyl, benzhydryl,

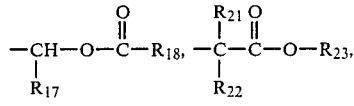

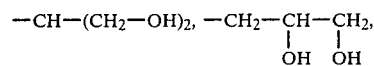

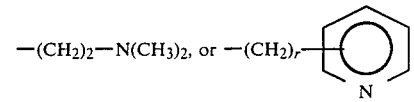

R$_{17}$ is hydrogen, lower alkyl, cycloalkyl or phenyl;
R$_{18}$ is hydrogen, lower alkyl, lower alkoxy, phenyl. or R$_{17}$ and R$_{18}$ taken together are

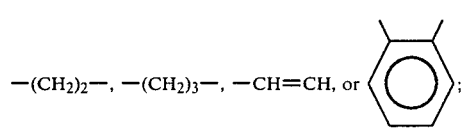

R$_{24}$ is hydrogen, lower alkyl,

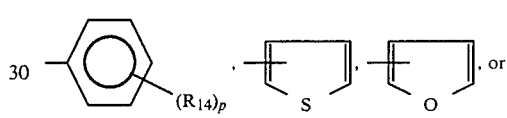

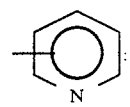

R$_{21}$ and R$_{22}$ are independently selected from the group consisting of hydrogen and lower alkyl; and
R$_{23}$ is lower alkyl.

2. A compound of claim 1 wherein:
R is hydrogen, straight or branched chain lower alkyl of 1 to 4 carbons, or phenyl;
R$_1$ is hydrogen, straight or branched chain lower alkyl of 1 to 4 carbons, CF$_3$,

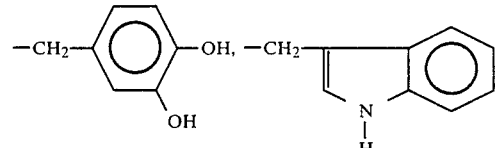

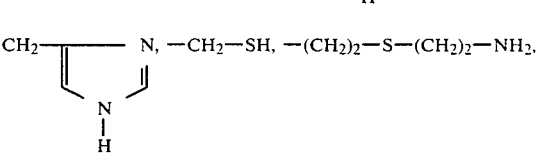

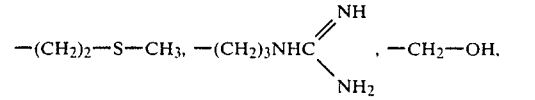

-continued

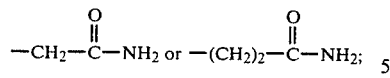

R4 is hydrogen, cyclohexyl, or phenyl;
R5 is hydrogen, straight or branched chain lower alkyl of 1 to 4 carbons,

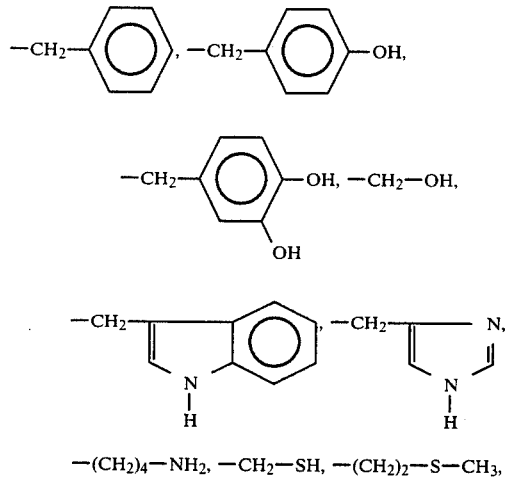

$-(CH_2)_4-NH_2$, $-CH_2-SH$, $-(CH_2)_2-S-CH_3$,

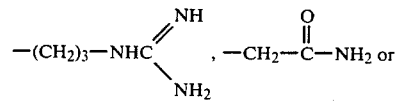

$-(CH_2)_2-\overset{O}{\underset{\|}{C}}-NH_2$;

R6 is hydrogen, straight or branched chain lower alkyl of 1 to 4 carbons, an alkali metal salt ion,

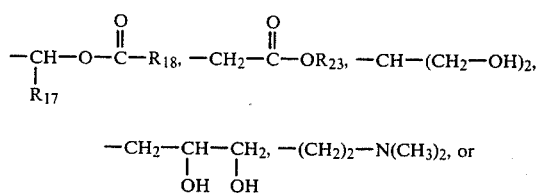

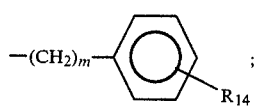

R17 is hydrogen, straight or branched chain lower alkyl of 1 to 4 carbons, or cyclohexyl;
R18 is straight or branched chain lower alkyl of 1 to 4 carbons or phenyl;
R23 is straight or branched chain lower alkyl of 1 to 4 carbons;
R2 is

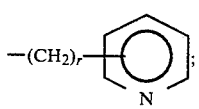

R3 is straight or branched chain lower alkyl of 1 to 4 carbons,

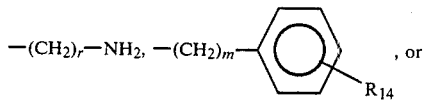

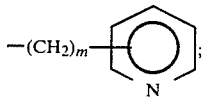

R7 is hydrogen, hydroxy, straight or branched chain lower alkyl of 1 to 4 carbons, cyclohexyl, amino, —O—lower alkyl wherein lower alkyl is straight or branched chain of 1 to 4 carbons,

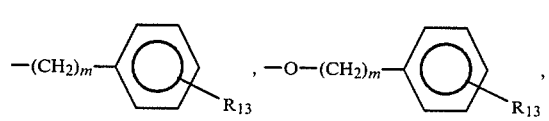

1-naphthyloxy, 2-naphthyloxy, —S—lower alkyl wherein lower alkyl is straight or branched chain of 1 to 4 carbons,

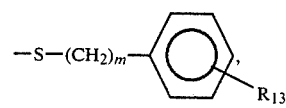

1-naphthylthio, or 2-naphthylthio;
R8 is —O—lower alkyl, —S—lower alkyl,

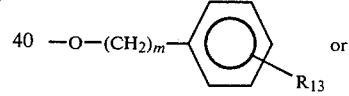

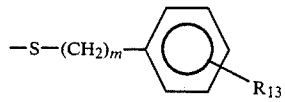

wherein lower alkyl is straight or branched chain of 1 to 4 carbons,
R9 is phenyl, 2-hydroxyphenyl or 4-hydroxyphenyl;
R10 are both fluoro, both chloro, or both —Y—R16; Y is O or S;
R16 is straight or branched chain lower alkyl of 1 to 4 carbons or the R16 groups join to complete an unsubstituted 5- or 6-membered ring or said ring in which one or more of the available carbons has a methyl or dimethyl substituent;
R11, R11', R12 and R12' are all hydrogen or R11 is phenyl, 2-hydroxyphenyl, or 4-hydroxyphenyl and R11', R12 and R12' are all hydrogen;
r is an integer from 1 to 4;
m is zero, one, or two;
R13 is hydrogen, methyl, methoxy, methylthio, chloro, bromo, fluoro, or hydroxy;
R14 is hydrogen, methyl, methoxy, methylthio, chloro, bromo, fluoro, or hydroxy; and
R24 is phenyl.

3. A compound of claim 2 wherein:
X is

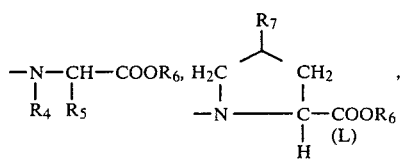

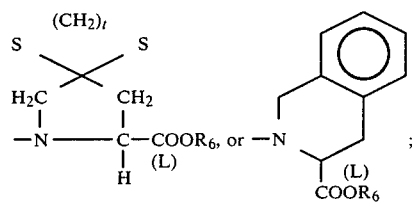

R is hydrogen or methyl;
$R_1$ is hydrogen, methyl, or —$(CH_2)_4$—$NH_2$;
$R_6$ is hydrogen, straight or branched chain lower alkyl or 1 to 4 carbons, or an alkali metal salt ion;
$R_4$ is cyclohexyl or phenyl and $R_5$ is hydrogen or $R_4$ is hydrogen and $R_5$ is methyl,

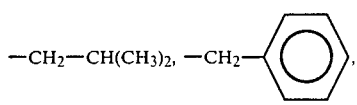

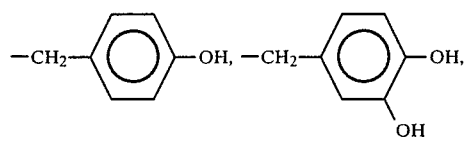

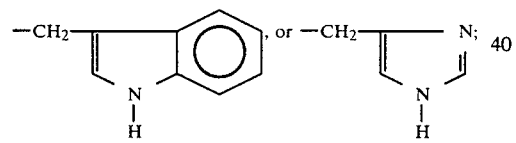

$R_7$ is hydrogen, cyclohexyl, lower alkoxy of 1 to 4 carbons,

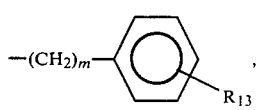

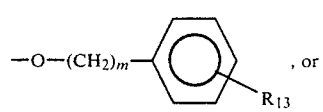

m is zero, one or two;
$R_{13}$ is hydrogen, methyl, methoxy, methylthio, chloro, bromo, fluoro, or hydroxy; and
t is 2 or 3.

4. A compound of claim 3 wherein
X is

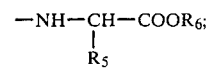

$R_2$ is phenyl; and
$R_3$ is methyl.

5. The compound of claim 4 wherein:
$R_5$ is —$CH_2$—$CH(CH_3)_2$;
$R_6$ is hydrogen;
R is hydrogen; and
$R_1$ is

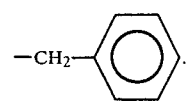

6. The compound of claim 5, (3S)-N-[N-[3-(benzoylamino)-2-hydroxybutyl]-L-phenylalanyl]-L-leucine, monohydrochloride, isomer A.

7. The compound of claim 5, (3S)-N-[N-[3-(benzoylamino)-2-hydroxybutyl]-L-phenylalanyl]-L-leucine, monohydrochloride, isomer B.

8. A compound of claim 3 wherein:
X is

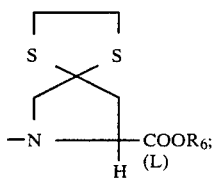

$R_2$ is phenyl; and
$R_3$ is

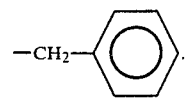

9. A compound of claim 3 wherein
X is

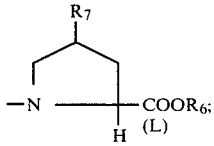

$R_2$ is phenyl; and
$R_3$ is

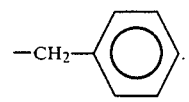

10. A compound of claim 9 wherein $R_7$ is hydrogen.
11. The compound of claim 10 wherein:
$R_6$ is hydrogen;
R is hydrogen; and $R_1$ is methyl.

12. The compound of claim 11, (3S)-1-[N-[3-(benzoylamino)-2-hydroxy-4-phenylbutyl]-L-alanyl]-L-proline, monohydrochloride.

13. The compound of claim 10 wherein:
$R_6$ is hydrogen;
R is methyl; and
$R_1$ is hydrogen.

14. The compound of claim 13, (3S)-1-[[[3-(benzoylamino)-2-hydroxy-4-phenylbutyl]-methylamino]acetyl]-L-proline, monohydrochloride, isomer A.

15. The compound of claim 13, (3S)-1-[[[3-(benzoylamino)-2-hydroxy-4-phenylbutyl]-methylamino]acetyl]-L-proline, monohydrochloride, isomer B.

16. The compound of claim 10 wherein:
$R_6$ is hydrogen;
R is hydrogen; and
$R_1$ is $-(CH_2)_4-NH_2$.

17. The compound of claim 16, (3S)-1-[N-[3-(benzoylamino)-2-hydroxy-4-phenylbutyl]-L-lysyl]-L-proline, dihydrochloride.

18. A compound of claim 9 wherein:
$R_7$ is $$-S-\text{C}_6\text{H}_5$$

19. The compound of claim 18 wherein:
$R_6$ is hydrogen;
R is methyl; and
$R_1$ is hydrogen.

20. The compound of claim 19, (4S)-1-[[[3-(benzoylamino)-2-hydroxy-4-phenylbutyl]methylamino]acetyl]-4-(phenylthio)-L-proline, monohydrochloride.

21. A pharmaceutical composition useful for treating hypertension comprising a pharmaceutically acceptable carrier and a hypotensive compound of the formula $$R_3-\underset{\underset{\underset{R_2}{C=O}}{\underset{|}{NH}}}{CH}-\overset{OH}{\underset{|}{CH}}-CH_2-\overset{R}{\underset{|}{N}}-\overset{R_1}{\underset{|}{CH}}-\overset{O}{\underset{\|}{C}}-X$$

wherein R, $R_1$, $R_2$, $R_3$ and X are as defined in claim 1.

22. The method of treating hypertension in a mammalian host which comprises administering an effective amount of the composition of claim 21.

23. A pharmaceutical composition useful as an analgesic comprising a pharmaceutically acceptable carrier and an enkephalinase inhibiting compound of the formula $$R_3-\underset{\underset{\underset{R_2}{C=O}}{\underset{|}{NH}}}{CH}-\overset{OH}{\underset{|}{CH}}-CH_2-\overset{R}{\underset{|}{N}}-\underset{(L)}{\overset{R_1}{\underset{|}{CH}}}-\overset{O}{\underset{\|}{C}}-NH-\underset{R_5}{\underset{|}{CH}}-COOR_6$$

wherein R, $R_1$, $R_2$, $R_3$, $R_5$ and $R_6$ are as defined in claim 1.

24. The method of relieving pain in a mammalian host which comprises administering an effective amount of the composition of claim 23.

* * * * *